United States Patent
Stango et al.

(10) Patent No.: US 10,888,292 B2
(45) Date of Patent: Jan. 12, 2021

(54) IMAGING WITH CURVED COMPRESSION ELEMENTS

(71) Applicant: HOLOGIC, INC., Marlborough, MA (US)

(72) Inventors: Timothy R. Stango, Marlborough, MA (US); Jay A. Stein, Marlborough, MA (US); Biao Chen, Marlborough, MA (US); Christopher Ruth, Marlborough, MA (US)

(73) Assignee: HOLOGIC, INC., Marlborough, MA (US)

( * ) Notice: Subject to any disclaimer, the term of this patent is extended or adjusted under 35 U.S.C. 154(b) by 0 days.

(21) Appl. No.: 16/348,343

(22) PCT Filed: Sep. 25, 2017

(86) PCT No.: PCT/US2017/053311
§ 371 (c)(1),
(2) Date: May 8, 2019

(87) PCT Pub. No.: WO2018/089118
PCT Pub. Date: May 17, 2018

(65) Prior Publication Data
US 2020/0069274 A1    Mar. 5, 2020

Related U.S. Application Data

(60) Provisional application No. 62/531,807, filed on Jul. 12, 2017, provisional application No. 62/419,336, filed on Nov. 8, 2016.

(51) Int. Cl.
*A61B 6/00* (2006.01)
*A61B 6/04* (2006.01)

(52) U.S. Cl.
CPC ............ *A61B 6/502* (2013.01); *A61B 6/0414* (2013.01); *A61B 6/5258* (2013.01); *A61B 6/4447* (2013.01); *A61B 6/582* (2013.01)

(58) Field of Classification Search
CPC ..... A61B 6/502; A61B 6/0414; A61B 6/5258; A61B 6/582
See application file for complete search history.

(56) References Cited

U.S. PATENT DOCUMENTS

| 3,971,950 A | 7/1976 | Evans et al. |
| 4,496,557 A | 1/1985 | Malen |
| (Continued) | | |

FOREIGN PATENT DOCUMENTS

| JP | S53-103672 U | 8/1978 |
| JP | 2015-027382 | 2/2015 |
| (Continued) | | |

OTHER PUBLICATIONS

International Search Report and Written Opinion of the International Searching Authority for International Patent Application No. PCT/US2017/053311 dated Mar. 6, 2018, 21 pages.

(Continued)

*Primary Examiner* — Chih-Cheng Kao

(57) ABSTRACT

A curved compression element, such as a breast compression paddle, and imaging systems and methods for use with curved compression elements. A system may include a radiation source, a detector, and a curved compression element. Operations are performed that include receiving image data from the detector; accessing a correction map for the at least one compression paddle; correcting the image data based on the correction map to generate a corrected image data; and generating an image of the breast based on the corrected image data. The breast compression element generally has no sharp edges, but rather has smooth edges and transitions between surfaces. The breast compression (Continued)

paddle also includes a flexible material that spans a portion of a curved bottom surface of the breast compression paddle to define a gap. The flexible material may be a thin-film material such as a shrink wrap.

10 Claims, 20 Drawing Sheets

(56) References Cited

U.S. PATENT DOCUMENTS

| | | | |
|---|---|---|---|
| 4,943,986 | A | 7/1990 | Barbarisi |
| 5,051,904 | A | 9/1991 | Griffith |
| 5,359,637 | A | 10/1994 | Webber |
| 5,506,877 | A | 4/1996 | Niklason |
| 5,553,111 | A | 9/1996 | Moore et al. |
| D376,012 | S | 11/1996 | Hixson, Sr. |
| 5,706,327 | A | 1/1998 | Adamkowski |
| 6,289,235 | B1 | 9/2001 | Webber |
| 6,647,092 | B2 | 11/2003 | Eberhard |
| 7,123,684 | B2 | 10/2006 | Jing et al. |
| 7,245,694 | B2 | 7/2007 | Jing et al. |
| 7,430,272 | B2 | 9/2008 | Jing et al. |
| 7,583,786 | B2 | 9/2009 | Jing et al. |
| 7,831,296 | B2 | 11/2010 | Defreitas |
| 7,869,563 | B2 | 1/2011 | Defreitas et al. |
| 8,175,219 | B2 | 5/2012 | DeFreitas et al. |
| 8,787,522 | B2 | 7/2014 | Smith et al. |
| 9,226,718 | B1 | 1/2016 | Baxley |
| 9,332,947 | B2 | 5/2016 | DeFreitas et al. |
| 9,782,135 | B2 | 10/2017 | Stango et al. |
| 10,603,002 | B2 | 3/2020 | Stango |
| 2001/0038861 | A1 | 11/2001 | Hsu |
| 2002/0061090 | A1 | 5/2002 | Lindstrom |
| 2004/0066882 | A1 | 4/2004 | Eberhard |
| 2004/0066884 | A1 | 4/2004 | Claus |
| 2004/0066904 | A1 | 4/2004 | Eberhard |
| 2004/0218727 | A1* | 11/2004 | Shoenfeld ............ A61B 6/0414 378/167 |
| 2005/0008117 | A1 | 1/2005 | Livingston |
| 2005/0063509 | A1 | 3/2005 | DeFreitas et al. |
| 2005/0113681 | A1 | 5/2005 | DeFreitas et al. |
| 2005/0113683 | A1 | 5/2005 | Lokhandwalla et al. |
| 2007/0223652 | A1 | 9/2007 | Galkin |
| 2007/0242794 | A1* | 10/2007 | Stanton ................ A61B 6/4233 378/5 |
| 2007/0280412 | A1 | 12/2007 | Defreitas et al. |
| 2008/0080668 | A1 | 4/2008 | Kashiwagi |
| 2009/0268865 | A1* | 10/2009 | Ren ........................ A61B 6/544 378/37 |
| 2010/0046698 | A1 | 2/2010 | Lebovic et al. |
| 2012/0277625 | A1 | 11/2012 | Nakayama |
| 2014/0296701 | A1 | 10/2014 | Hancu et al. |
| 2015/0282770 | A1 | 10/2015 | Klanian et al. |
| 2016/0081633 | A1 | 3/2016 | Stango et al. |
| 2016/0242707 | A1 | 8/2016 | Defreitas et al. |
| 2017/0340303 | A1 | 11/2017 | Stango |
| 2018/0165840 | A1* | 6/2018 | Bernard ................ A61B 6/022 |

FOREIGN PATENT DOCUMENTS

| | | |
|---|---|---|
| KR | 10-2011-0089446 | 8/2011 |
| KR | 10-2014-0058066 | 5/2014 |
| WO | 2010/028208 | 3/2010 |
| WO | 2010/102087 | 9/2010 |
| WO | 2014/074602 | 5/2014 |
| WO | 2014/176445 A2 | 10/2014 |
| WO | 2015/054518 A1 | 4/2015 |
| WO | 2016/073445 | 5/2016 |
| WO | 2018/089118 | 5/2018 |

OTHER PUBLICATIONS

Digital Clinical Reports, Tomosynthesis (GE Brochure 98-5493, Nov. 1998), 8 pgs.
European Extended Search Report in Application 15857678.5, dated Jun. 26, 2018, 8 pages.
Grant, D.G., "Tomosynthesis: a three-dimensional imaging technique", IEEE Trans. Biomed. Engineering, vol. GME-19, #1, (Jan. 1972), pp. 20-28.
PCT International Preliminary Report on Patentability in International Application PCT/US2015/058782, dated May 18, 2017, 10 pgs.
PCT International Search Report and Written Opinion of the International Searching Authority for corresponding International Patent Application No. PCT/US2015/058782 dated Feb. 17, 2016, 14 pgs.
PCT International Search Report and Written Opinion of the International Searching Authority for International Patent Application No. PCT/US2018/046304 dated Dec. 11, 2018, 18 pages.
PCT International Search Report and Written Opinion of the International Searching Authority for International Patent Application No. PCT/US2018/046312 dated Dec. 11, 2018, 14 pages.
U.S. Appl. No. 60/628,516 entitled "Matching geometry generation and display of mammograms and tomosynthesis images", filed Nov. 15, 2004, 20 pgs.

* cited by examiner

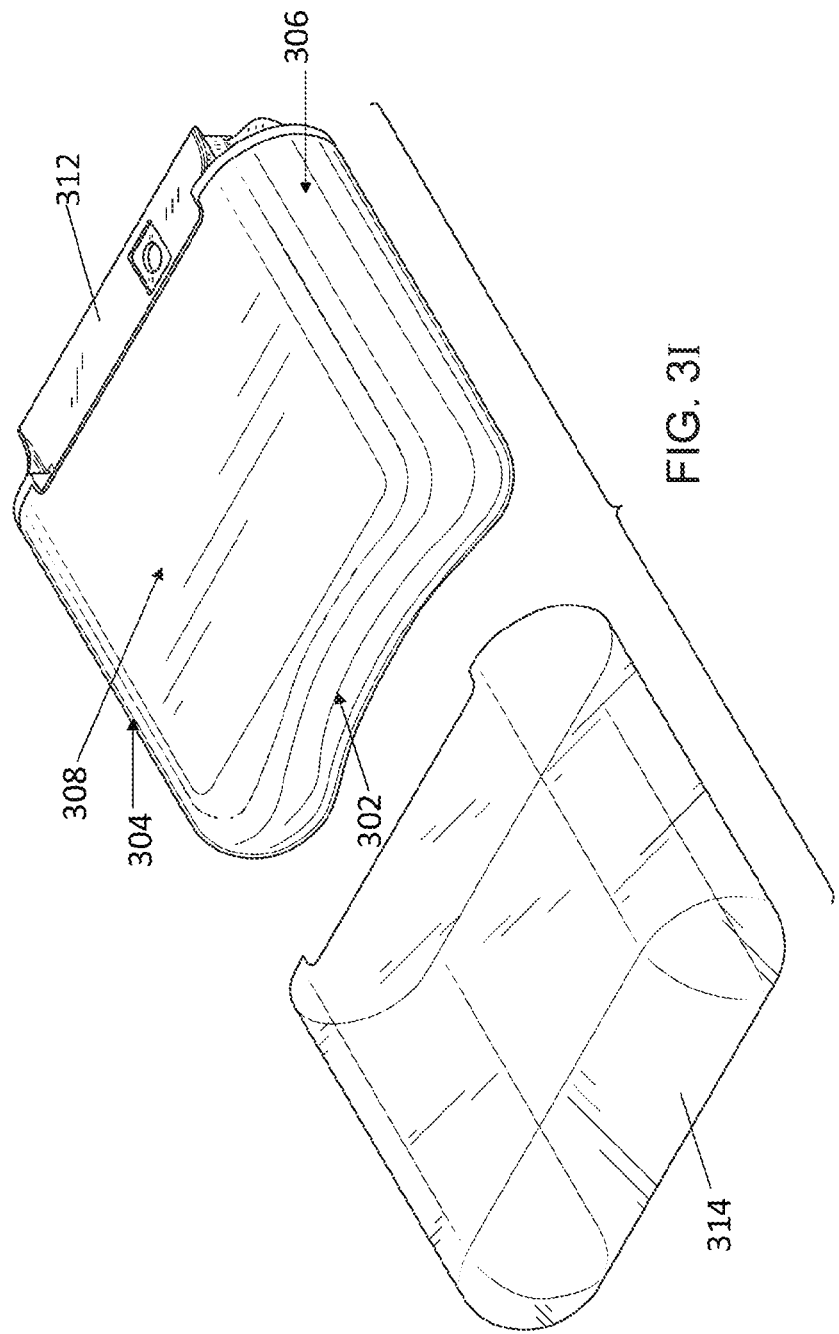

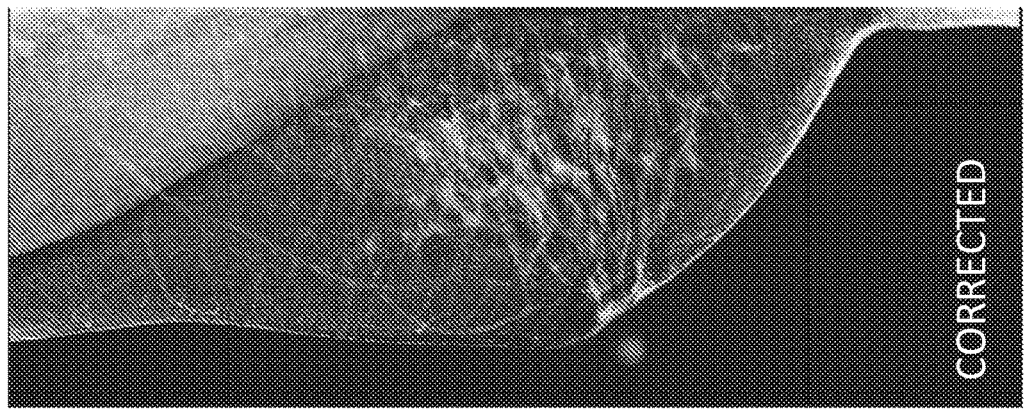
FIG. 5B CORRECTED
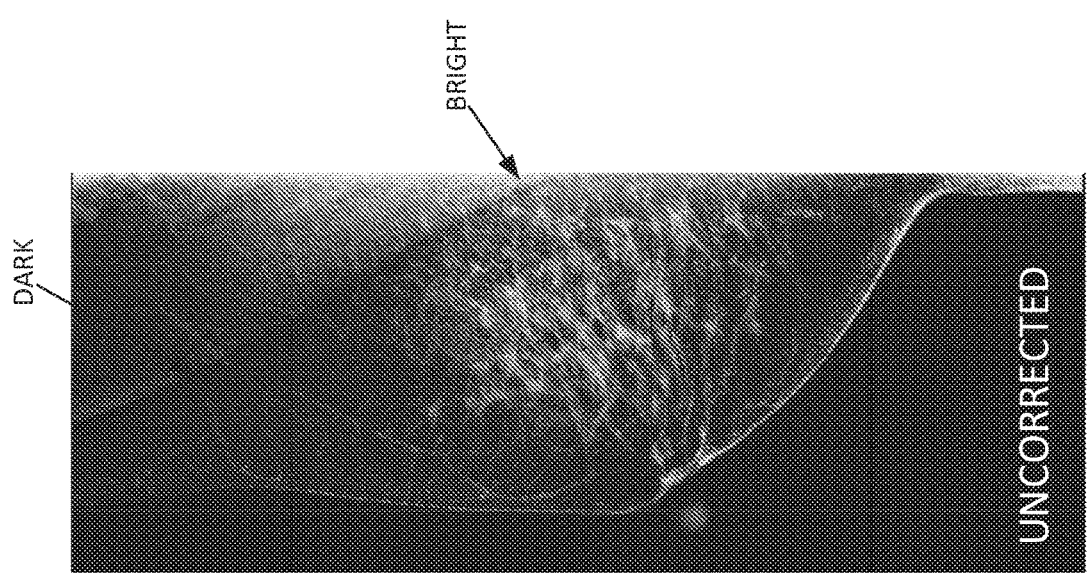
FIG. 5A UNCORRECTED

IMAGING WITH CURVED COMPRESSION ELEMENTS

CROSS-REFERENCE TO RELATED APPLICATIONS

This application is a National Stage Application of PCT/US2017/053311, filed on Sep. 25, 2017, which claims priority to: (1) U.S. Provisional Application No. 62/419,336, titled "Breast Compression Paddle" and filed on Nov. 8, 2016, and (2) U.S. Provisional Application No. 62/531,807, titled "Image Processing For Curved Paddles" and filed on Jul. 12, 2017, both of which are incorporated by reference in their entireties. To the extent appropriate, a claim of priority is made to each of the above disclosed applications.

BACKGROUND

A significant patient concern in mammography and breast tomosynthesis is the discomfort the patient may feel when the breast is compressed, typically between two rigid plastic surfaces, with sufficient force to immobilize the breast and spread out the breast tissues for x-ray imaging. Another significant challenge is to ensure that the imaged field include the desired amount of breast tissue. The reasons for using compression include: (1) to make the breast thinner in the direction of x-ray flux and thereby reduce patient radiation exposure from the level required to image the thicker parts of a breast that is not compressed; (2) to make the breast more uniform in thickness in the direction of x-ray flux and thereby facilitate more uniform exposure at the image plane over the entire breast image; (3) to immobilize the breast during the x-ray exposure and thereby reduce image blurring; and (4) to bring breast tissues out from the chest wall into the imaging exposure field and thus image more tissue. As the breast is being compressed, typically a technician manipulates the breast to position it appropriately and counter the tendency that compression has of pushing breast tissue toward the chest wall and out of the image field.

Standard compression methods for mammography and tomosynthesis use a movable, rigid clear plastic compression paddle. The breast is placed on a breast support platform that typically is flat, and the paddle is then compressed onto the breast, usually while a technician or other health professional is holding the breast in place and perhaps manipulates the breast to ensure proper tissue coverage in the image receptor's field of view and to help spread the breast.

SUMMARY

In an aspect, the technology relates to a system for imaging a breast. The system includes a radiation source; at least one compression paddle having a non-planar compression surface, wherein the at least one compression paddle is configured to compress the breast during imaging of the breast; a detector configured to detect radiation emitted from the radiation source after passing through the at least one compression paddle and the breast, wherein the detector includes a plurality of pixels; and a memory and a processor operatively connected to the detector, wherein the memory stores instructions that, when executed by the processor, perform a set of operations. The operations include receiving image data from the detector; accessing a correction map for the at least one compression paddle; correcting the image data based on the correction map to generate a corrected image data; and generating an image of the breast based on the corrected image data. In an example, the operations further include at least two of the following operations: upscaling the correction map based on an image size for the image; modifying the correction map by applying a squeeze factor; modifying the correction map for a projection angle and a paddle shift; and modifying the correction map based on a magnification. In another example, modifying the correction map based on magnification is based at least in part on a height of the compression paddle. In yet another example, the correction map is represented as a matrix, wherein the elements of the matrix represent correction values for a corresponding pixel of the detector. In still yet another example, wherein the elements of the matrix include values for scaling a brightness value of the corresponding pixel of the detector.

In another example, correcting the image data includes correcting the image data on a pixel-by-pixel level. In yet another example, the operations further include further correcting a chest-wall area of the image representative of an area within about 2 cm of a chest wall. In still yet another example, correcting the chest-wall area of the image includes determining a delta value based on at least a slope value and a threshold value.

In another example, the correction map is generated by a process including: filling the compression paddle with a liquid to create a filled paddle; placing the filled paddle on a substantially radiolucent surface, wherein the radiolucent surface covers an imaging area of a detector; passing radiation through the filled paddle and substantially radiolucent surface; detecting the radiation passed through the filled paddle and substantially radiolucent surface; generating a correction image based on the detected radiation; identifying an average pixel value over the correction image; and generating the correction map by dividing each pixel in the correction image by the average pixel value. In yet another example, generating the correction map further comprises generating a series of polynomial fits to represent the correction map.

In another aspect, the technology relates to a method including: filling a hollow paddle with a liquid to create a filled paddle; placing the filled paddle on a substantially radiolucent surface, wherein the radiolucent surface covers an imaging area of a detector; passing radiation through the filled paddle and substantially radiolucent surface; detecting the radiation passed through the filled paddle and substantially radiolucent surface; generating a correction image based on the detected radiation; identifying an average pixel value over the correction image; and generating a correction map by dividing each pixel in the correction image by the average pixel value. In an example, the method further comprises generating a series of polynomial its to represent the correction map. In another example, generating the series of polynomial fits comprises: for each image column (x) of the detector, selecting points along rows (y) of the detector; and fitting the selected points to a polynomial function to generate a set of fitted points; and wherein generating the correction map further includes generating a fitted image based on the fitted points. In yet another example, the polynomial function is a fourth-order polynomial. In still yet another example, generating the correction map further comprises: smoothing the fitted image using a boxcar averaging method; and scaling down the fitted image using decimation. In another example, the liquid is water and the substantially radiolucent material is a Lucite block having a thickness of approximately 4 cm.

In yet another aspect, the technology relates to a computer-implemented method for generating an image of a breast. The method includes receiving image data from a radiographic detector; accessing a correction map for at least one compression paddle having a non-planar compression surface; correcting the image data based on the correction map to generate corrected image data; and generating the image of the breast based on the corrected image data. In an example, the method further includes at least two of: upscaling the correction map based on an image size for the image; modifying the correction map by applying a squeeze factor; modifying the correction map for a projection angle and a paddle shift; and modifying the correction map based on a magnification. In another example, the correction map is a matrix, and the elements of the matrix represent correction values for a corresponding pixel of the detector. In yet another example, wherein correcting the image data includes correcting the image data on a pixel-by-pixel level.

In one aspect, the technology relates to a breast compression paddle for use in an imaging system, the breast compression paddle having: a curved right surface; a curved left surface; a curved bottom surface; a curved front surface; a top surface; and a flexible material in contact with the curved right surface, the curved left surface, the curved front surface, and the top surface, wherein the flexible material is spaced apart from at least a portion of the curved bottom surface.

In one aspect, the technology relates to a breast compression paddle for use in an imaging system, the breast compression paddle having: a curved right surface; a curved left surface; a curved bottom surface; a curved front surface; a top surface; and a transition between adjacent ones of the curved right surface, the curved left surface, the curved bottom surface, the curved front surface, and the top surface, wherein all transitions include no sharp edges.

In one aspect, the technology relates to an imaging system having: an imaging source; an imaging receptor; and a breast compression element having: a plurality of curved side surfaces; a front surface connected to each of the plurality of curved side surfaces with a smooth transition between; a compression surface connecting the plurality of curved side surfaces; and a non-compression surface disposed opposite the compression surface and connecting the plurality of curved side surfaces.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF UTE DRAWINGS

FIG. 3I depicts an exploded perspective view of the breast compression element of FIG. 3A.

FIG. 5A depicts an example image without the image processing techniques discussed herein.

FIG. 5B depicts an example image with the image processing techniques discussed herein.

DETAILED DESCRIPTION

Figure 1A:
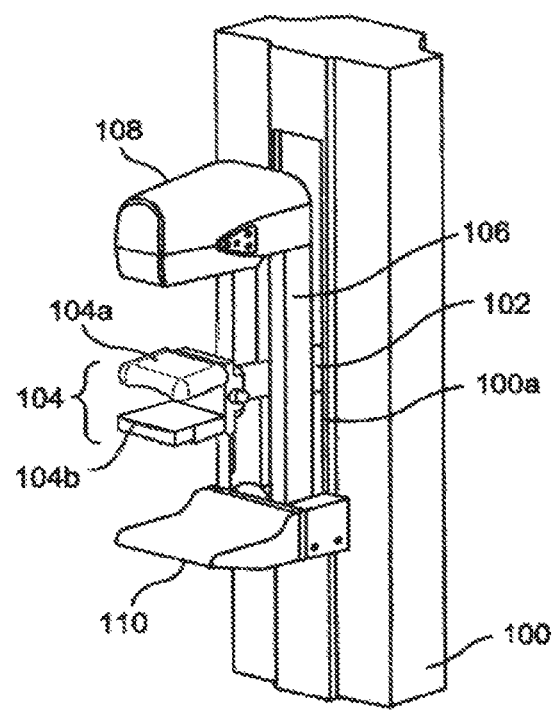
FIG. 1A depicts a perspective view of a portion of an upright breast x-ray imaging system.

The present technology relates to a breast compression element, such as a breast compression paddle or compression support surface, for use in a breast imaging system. During imaging of a breast, it is often desirable to immobilize the breast through compression. For instance, by compressing the breast, the breast can be made thinner requiring a lower dose of radiation. Further, by immobilizing the breast, image blurring from movement of the breast during imaging is reduced. Other benefits are also realized by compressing the breast. The paddle commonly used to compress the breast, however, may cause distortions in the imaging process as x-rays must pass through the paddle. For instance, while the compression paddles are generally made from at least partially radiolucent materials, the shape and configuration of the compression paddles may cause deflection, refraction, dispersion, reflection, or other undesired interference with an x-ray beam as it passes through the paddle. Thus, undesired artifacts may appear in the resultant image or may need to be accounted for during image processing.

The paddle may also cause discomfort to the patient whose breast is being compressed. One reason for discomfort that the patient may feel is that the compression force is non-uniformly distributed throughout the breast. It is concentrated at the thickest portion of the breast, usually near the chest wall, at or near the lower front edge of the compression paddle and the upper front corner of the breast platform. The anterior portion of the breast, such as near the nipple, may receive less compressive force, or no compressive force. The paddle may not even contact this portion of the breast, (The terms front, lower, and upper pertain to using a craniocaudal (CC) imaging orientation, with the patient facing the front of the imaging system, although it should be understood that other imaging orientations, including mediolateral oblique (MLO) image orientations or views, are used with the same equipment and these terms need to be adjusted accordingly.)

To improve these issues relating to compression elements, in part, the breast compression elements discussed herein reduce or minimize sharp edges (e.g., no sharp edges), thus reducing image blurring due to edge effects. Further, the breast compression elements are shaped so as to have a more consistent thickness at all angles during imaging. Additionally or alternatively, a thin material spans a curved bottom surface of the breast compression element to create a gap between at least a portion of the bottom surface and the thin material. For example, the thin material may be a flexible thin film material displaying very limited stretching capability and strong tensile strength. As the breast compression element is pressed against the breast, the flexible material contacts the breast first so as to begin compression of the breast. As compressive pressure increases, the flexible material is deflected towards the curved bottom surface, providing a more comfortable compression process for the patient. The design of the breast compression structure also allows for more comfort and support in imaging systems that allow patients to tilt against the system.

Figure 1B:
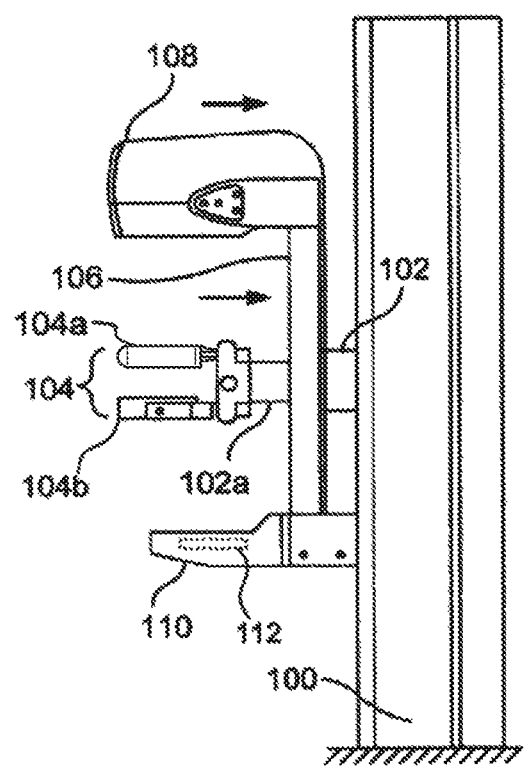
FIG. 1B depicts a side elevation of the system of FIG. 1A.
Figure 1C:
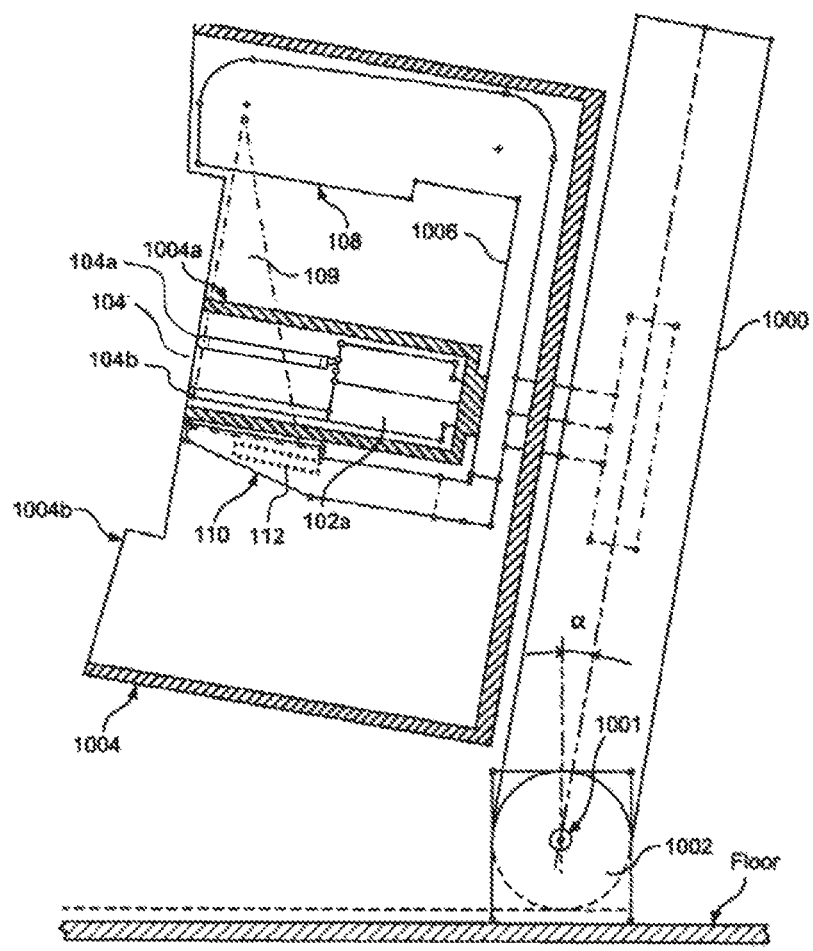
FIG. 1C depicts a side elevation of an example of a tilting imaging system.

FIGS. 1A-1C illustrate non-limiting examples of multi-mode breast x-ray imaging systems operable in a computed tomography (CT) mode but also configured to selectively operate in a tomosynthesis mode, including a wide angle tomosynthesis mode and a narrow angle tomosynthesis mode, as well as in a mammography mode. For clarity of illustration, a patient shield for use in the CT mode is omitted from FIGS. 1A-1B, but an example is illustrated in FIG. 1C. A support column 100 is secured to a floor and houses a motorized mechanism for raising and lowering a horizontally extending axle 102, which protrudes through an opening 100*a* in column 100, and for rotating axle 102 about its central axis. Axle 102 in turn supports a coaxial axle 102*a* that can rotate with or independently of axle 102. Axle 102 supports a breast immobilization unit comprising an upper compression element 104*a* and a lower compression element 104*b* such that each compression element can move up and down along the long dimension of support 100 together with axles 102 and 102*a*. At least one of the compression elements can move toward the other, and unit 104 can rotate about the common central axis of axles 102 and 102*a*. Either one or both of the upper compression element 104*a* and the lower compression element 104*b* may incorporate the breast compression element discussed herein and shown in FIGS. 3A-3I. The breast compression element discussed herein is depicted in FIG. 1A as in the upper position. In addition, axle 102 supports a gantry 106 for two types of motorized movement: rotation about the central axis of axle 102, and motion relative to axle 102 along the length of gantry 106. Gantry 106 carries at one end an x-ray source such as a shrouded x-ray tube generally indicated at 108, and at the other end a receptor housing 110 enclosing an imaging x-ray receptor.

When operating in a CT mode, the systems of FIGS. 1A-1C immobilize a patient's breast between compression elements 104*a* and 104*b*. Unit 104 is raised or lowered together with axle 102 to the height of the breast while the patient is upright, e.g., standing or sitting. The patient leans toward unit 104 from the left side of the system as seen in FIG. 1B, and a health professional, typically an x-ray technician, adjusts the breast between compression elements 104*a* and 104*b* while pulling tissue to the right in FIG. 1B and moving at least one of compression elements 104*a* and 104*b* toward the other to immobilize the breast and keep it in place, with as much as practicable of the breast tissue being between the compression elements 104*a* and 104*b*, In the course of taking x-ray measurements representing CT projection x-ray images CTp, from which to reconstruct images CTr of respective breast slices, gantry 106 rotates about the central axis of axle 102 while the breast remains immobilized in unit 104, imaging x-ray receptor 112 inside housing 110 may remain fixed relative to x-ray tube 108 during the rotation of gantry 106. In another example, the x-ray receptor 112 may rotate or pivot within the housing 110. A pyramid shaped beam of x-rays from tube 108 traverses the breast immobilized in unit 104 and impinges on imaging receptor 112, which in response generates a respective two-dimensional array of pixel values related to the amount of x-ray energy received for each increment of rotation at respective pixel positions in an imaging plane of the receptor. These arrays of pixel values for images CTp are delivered to and processed by a computer system to reconstruct slice images CTr of the breast. Gantry 106 may be configured for motorized movement toward column 100, to facilitate the x-ray technician's access to the patient's breast for positioning the breast in unit 104, and away from column 100 to ensure that x-ray tube 108 and imaging receptor 112 inside housing 110 can image the appropriate breast tissue. Alternatively, gantry 106 can maintain a fixed distance from column 100, to the left of the position seen in FIG. 1A, so that the imaging x-ray beam can pass through as much as practical of the breast immobilized in unit 104, in which case there would be no need for a mechanism to vary that distance.

FIG. 1C includes many of the same elements, components, and functionality as the example depicted in FIGS. 1A and 1B. Additionally, FIG. 1C includes a column 1000 that pivots from a vertical position about a pivot axis 1001 of a pivoting support 1002, for example over an angle α as illustrated. The angle α may be up to about 5°, up to about 10°, up to about 15°, or higher. This pivoting allows the patient to lean forward against a shield 1004, which may increase patient comfort and protect the patient from the rotating components. A rotating C-arm 1006 can carry an x-ray source 108 emitting x-ray beam 109, and an x-ray imaging receptor housing 110, and can be moved up and down column 1000 to accommodate patients of different heights. Shield 1004 shields the patient from the x-ray source 108 as it rotates around breast compression unit 104, and also shields the patient from any rotation of x-ray imaging receptor housing 110 containing an imaging receptor 112. Shield 1004 further acts to stabilize the patient leaning against it, and may include handles that the patient may hold to further facilitate patient comfort and stability. Shield 1004 can surround the rotational trajectory of source 108 and housing 110, and may include a front portion 1004*b* that has an opening for the patient's breast, which opening may be sufficiently large to allow a health professional to reach in to adjust the breast as it is being compressed. Shield 1004*a* surrounds compression unit 104 that may include two compression elements 104*a*, 104*b*, as discussed above. Shield 1004*a* may also include a portion 1004*b* that also protects the patient from motion of gantry 1006. Some or all of portion 1004*b* may be removable, particularly for taking mammograms. Further, as the patient leans against the imaging system, the patient also directly applies her weight against the breast compression unit 104.

Figure 2:
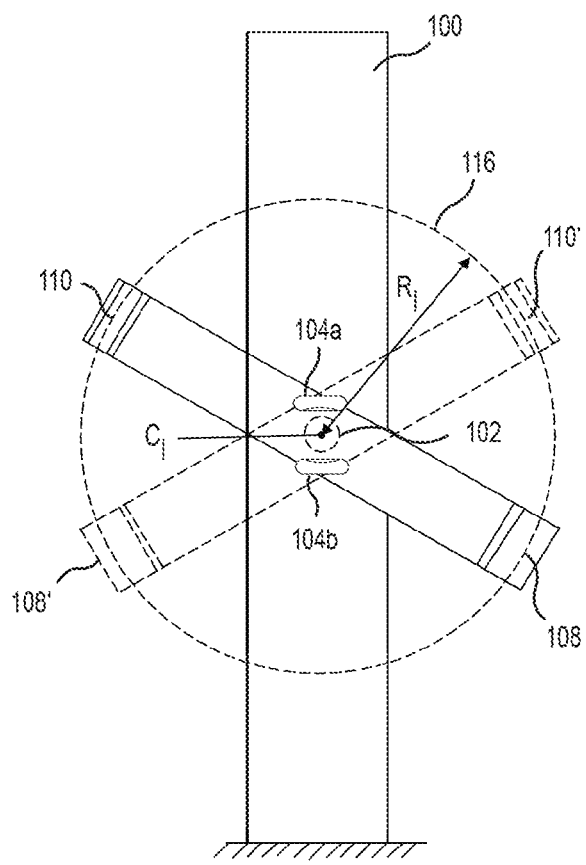
FIG. 2 depicts a front elevation an imaging system showing rotational movement of a radiation source.

FIG. 2 depicts a front elevation an imaging system showing rotational movement of a radiation source. CT scanning typically involves a rotation of the source 110 and receptor 108 through an angle of about 180° plus the angle subtended by the imaging x-ray beam, and in certain examples a rotation through a greater angle, e.g., about 360°, as shown in FIG. 2. Tomosynthesis scans similarly involve rotation of the source 110, although generally across a smaller angle, such as about 15°. The source 110 and receptor 108 rotate around breast about the central axis of the axle 102. The path along which the source 110 and the receptor 108 rotate may be called an imaging arc 116. The imaging arc 116 has a radius $R_I$ that extends from a center point $C_I$ which is located at the central axis of the axle 102 to the source, such as the x-ray tube 108. As such, a simplified representation of the of curvature ($k_I$) of the imaging arc 116 is $1/R_I$. In practice, the rotation may only be performed over a portion of the imaging arc 116, but the radius $R_I$, center point $C_I$, and curvature ($k_I$) of the arc 116 remains the same. Another position of the source 110' and the receptor 108' are depicted in FIG. 2 for illustrative purposes.

As discussed above, a challenge in upright breast CT and/or tomosynthesis is how to immobilize the breast. In some cases, for various reasons, little or no compression of the breast may be desirable. In other cases, it may be desirable to compress or otherwise act on the breast, for example so that breast tissue can be pulled away from patient's chest wall and securely retained in unit 104 for imaging. Accordingly, and to generally increase patient comfort, one or both of compression elements 104a and 104b are shaped in a manner designed to hold the breast for CT and/or tomosynthesis imaging while keeping the breast shaped so as to allow for close to equal path lengths of x-rays at least within individual slices. For example, the compression elements 104a and 104b may have, on the compression surfaces of the elements 104a, 104b, a curvature in the shape of an arc that shares the same center point $C_I$ as the imaging arc 116. This curvature is depicted more clearly in FIG. 3C. In such an example, the arc of the compression surface and the imaging arc 116 are concentric. In another example, the curvature of the compression surfaces of the compression elements 104a and 104b substantially matches the curvature of the imaging arc 116. In some examples, the curvature of the compression surfaces may be greater than or less than the curvature of the imaging arc 116. Compression elements 104a and 104b may be removably secured via a bracket so that different sets of compression elements can be used to accommodate differently sized or shaped breasts. Different degrees of breast compression can be used as selected by a health professional operating the systems described herein.

An example of a breast compression element 300 is shown in multiple views shown in FIGS. 3A-3I. FIGS. 3A-3I are described concurrently. The breast compression element 300 may be utilized as a breast compression paddle or surface or a breast support platform. In general, surfaces of the breast compression element 300 are described as depicted in the figures (e.g., "top," "bottom," "left," etc.). These general terms are utilized for clarity only to distinguish the various surfaces from each other. For instance, in FIGS. 3A-3I, the compression surface may be referred to as the bottom surface 318 and the non-compression surface may be referred to as the top surface 308. The breast compression element 300 includes a curved front surface 302, a curved left surface 304, a curved right surface 306, a top surface 308, a back surface 310, and a curved bottom surface 318. The breast compression element 300 may be manufactured from a material that is designed to cause minimal interference with the radiation beam passing through the breast compression element 300, such as a radiolucent material. For example, the breast compression element 300 may be made from a polycarbonate material, a carbon fiber material, or other similar materials. The breast compression element 300 may be hollow, solid, or partially filled. The back surface 310 of the breast compression element 300 is attached to a bracket 312. The bracket 312 may then be removably attached to an imaging system, as discussed above. The bracket 312 and/or a surface of the compression element 300 may have a gas inlet port 313 that is in fluidic communication with an interior of the compression element 300. Heated fluid, such as warm air or gas, may be injected into the compression element 300 via the gas inlet port to warm the compression element 300 before and/or during contact with the breast. Certain compression elements 300 may define a plurality of ports to allow the fluid to escape into a gap 316 between a flexible material 314 and the more rigid structure of the breast compression element 300.

In some implementations, the breast compression element 300 is surrounded by a flexible material 314. The flexible material 314 is generally a thin-film material and may be made from a variety of materials, e.g., a shrink-wrap material. In some examples, the flexible material 314 has a high tensile strength and limited stretching characteristics when surrounding the breast compression element 300. In an example, the flexible material 314 is in contact with and surrounds the right surface 306, the left surface 304, and the top surface 308. In such an example, the flexible material 314 spans from the right surface 306 to the left surface 304, defining a gap 316 between the flexible material 314 and the bottom surface 318. For instance, the flexible material 314 is spaced apart from the concave bottom surface 318 to define the gap 316. When the flexible material 314 spans from the right surface 306 to the left surface 306, the flexible material 314 is tensioned such that the portion of the flexible material 314 spaced apart from the concave bottom surface 318 is less flexible then when in a non-tensioned state, but without being rigid. In some examples, the flexible material 314 also surrounds the curved front surface 302. The flexible material 314 may also surround at least a portion of the back surface 310.

In operation, the breast compression element 300 is pressed against the breast such that the flexible material 314 first contacts the breast. In one embodiment, as the breast compression element 300 continues to compress the breast, the breast forces the flexible material 314 closer to the bottom surface 318 until the flexible material ultimately contacts the bottom surface 318, thus eliminating the gap 316. By having the flexible material 314 first contact the breast, patient comfort may increase and a more uniform compression may be achieved as the flexible material 314 contours to the shape of the breast during compression.

Figure 3A:
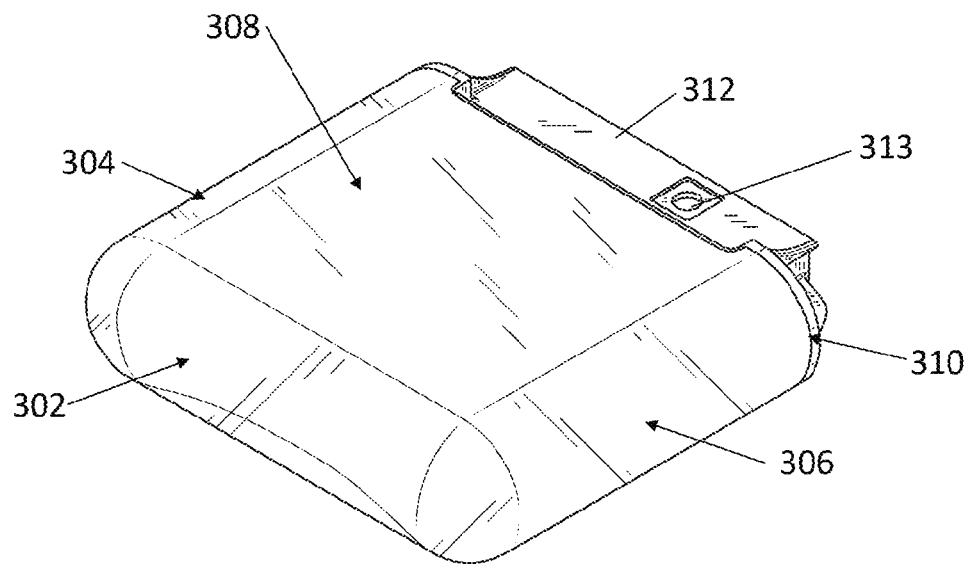
FIG. 3A depicts a top perspective view of a breast compression element.
Figure 3B:
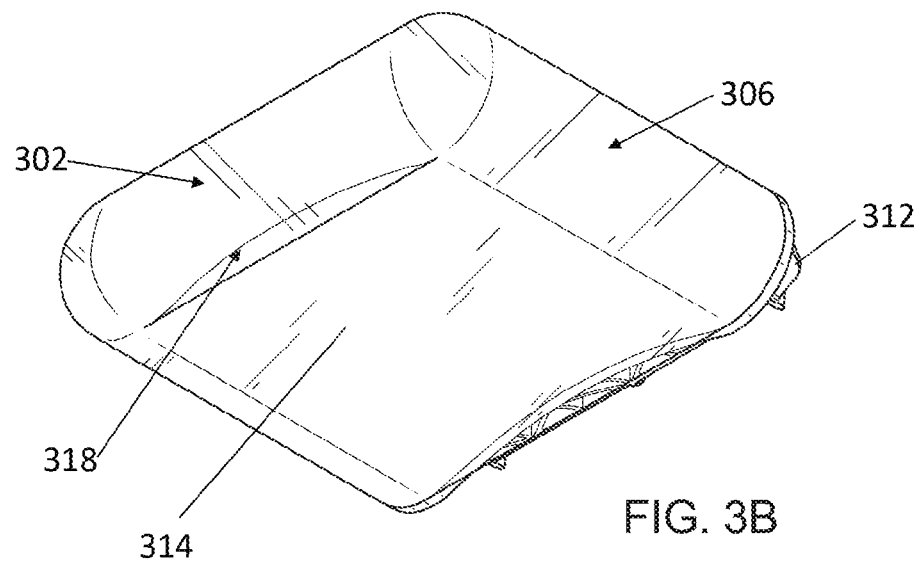
FIG. 3B depicts a bottom perspective view of the breast compression element of FIG. 3A.
Figure 3C:
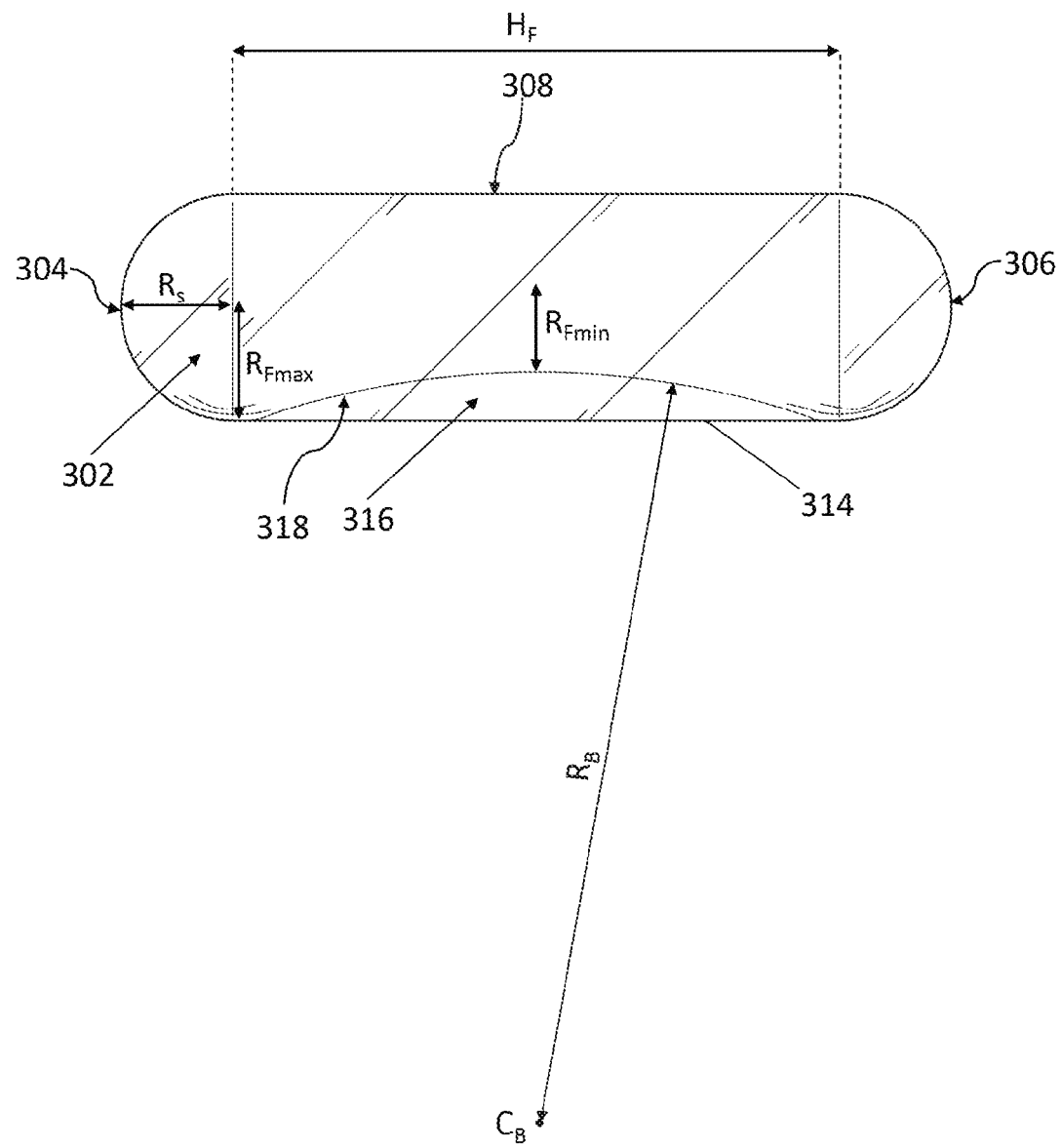
FIG. 3C depicts a front view of the breast compression element of FIG. 3A.
Figure 3D:
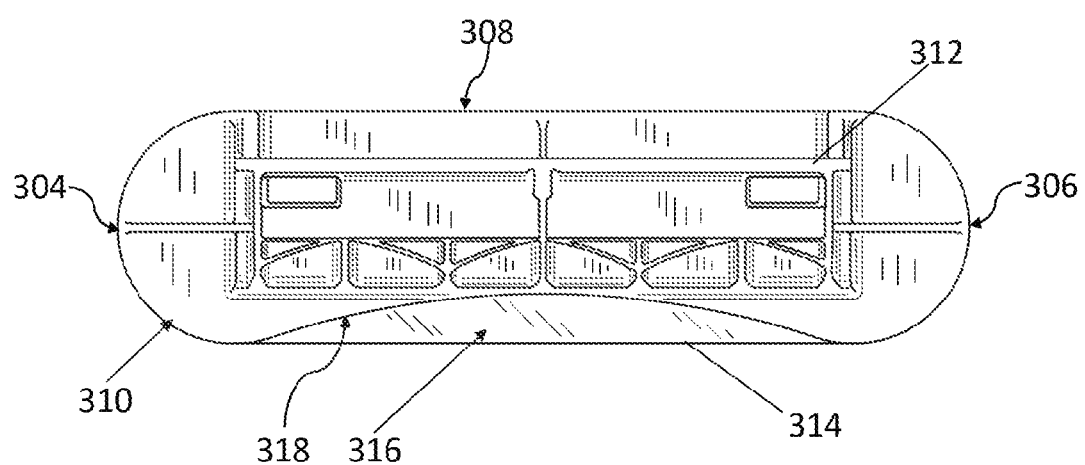
FIG. 3D depicts a back view of the breast compression element of FIG. 3A.
Figure 3E:
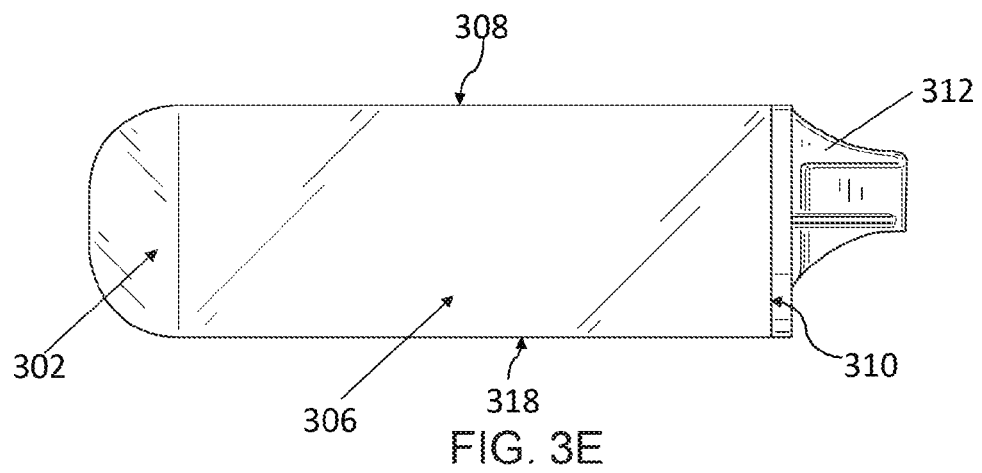
FIG. 3E depicts a right side view of the breast compression element of FIG. 3A.
Figure 3F:
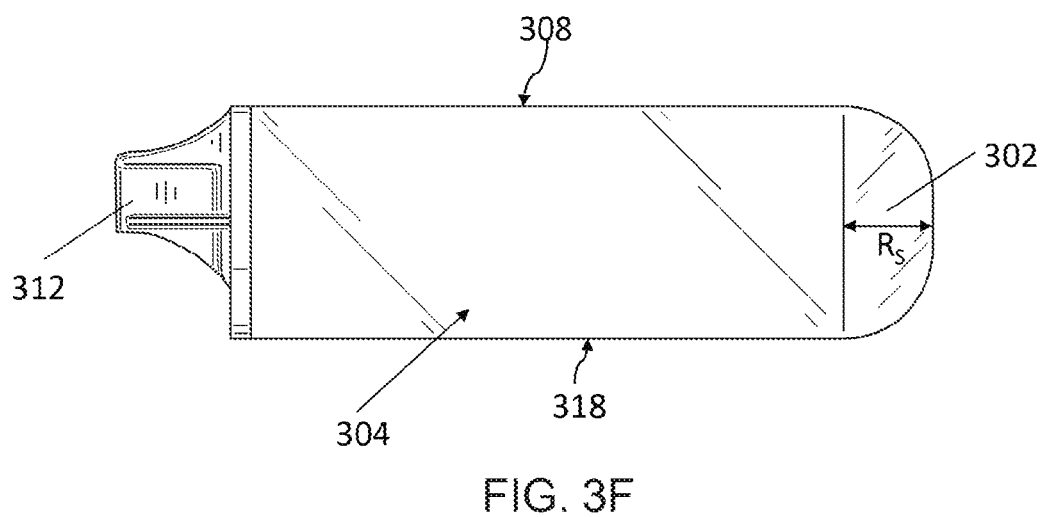
FIG. 3F depicts a left side view of the breast compression element of FIG. 3A.
Figure 3G:
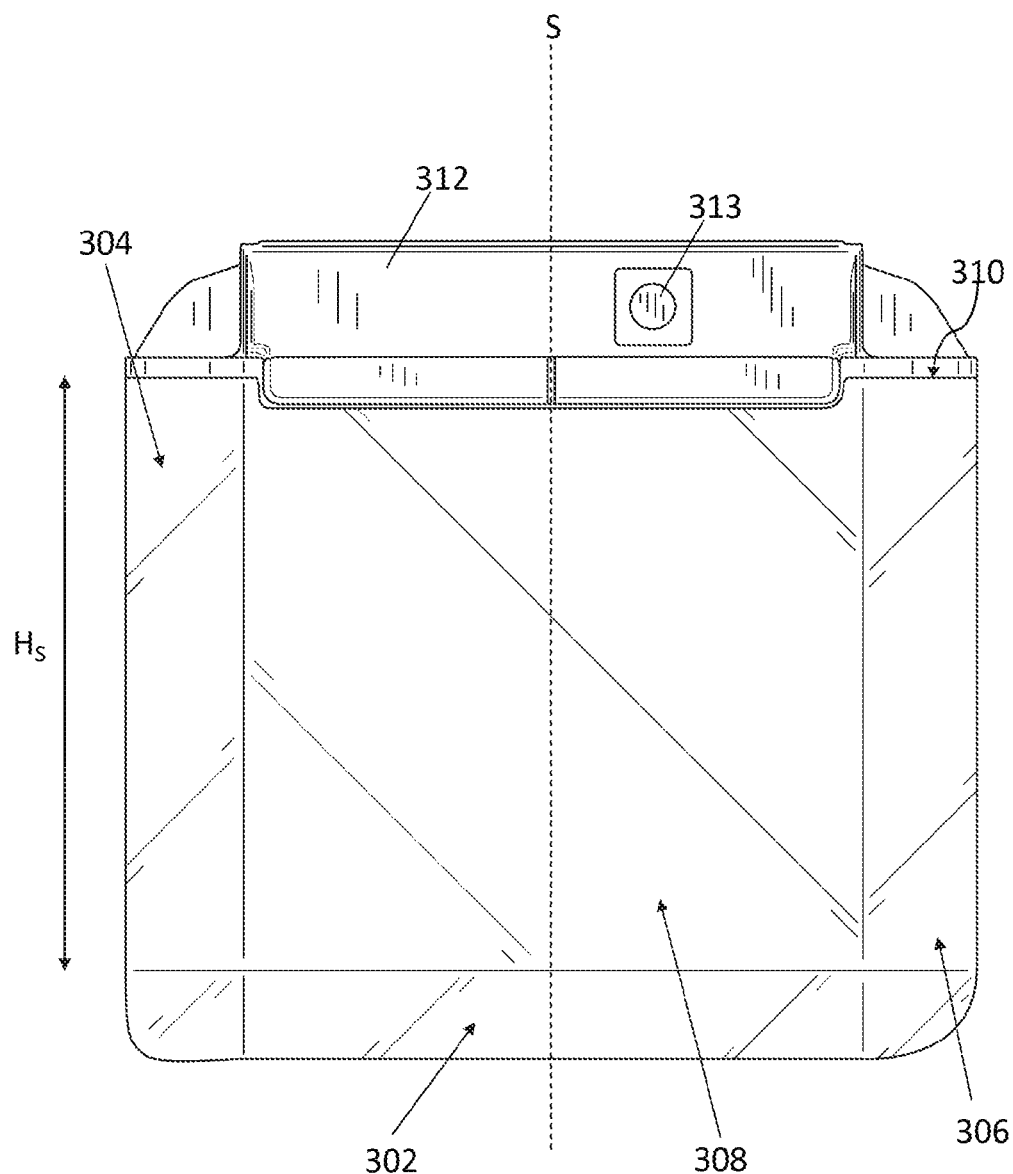
FIG. 3G depicts a top view of the breast compression element of FIG. 3A.
Figure 3H:
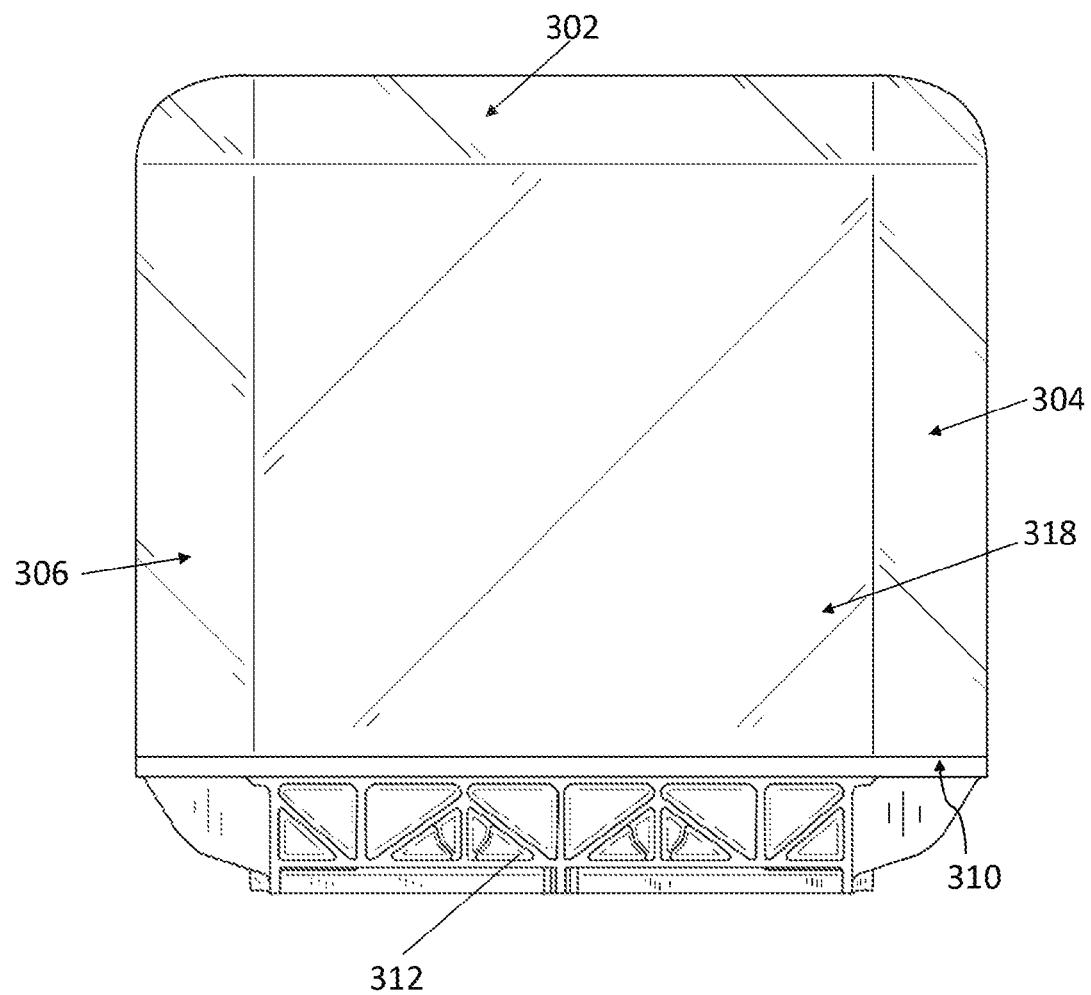
FIG. 3H depicts a bottom view of the breast compression element of FIG. 3A.

The shape of the breast compression element 300 also provides additional benefits in imaging systems. As can be seen from FIGS. 3A-3I, the breast compression element 300 is substantially symmetric about plane S, shown in FIG. 3G. The left surface 304 and the right surface 306 are generally semicylindical. The height $H_S$ of the semicylindrical shape of the left surface 304 and the right surface 306 is defined by the back surface 310 and the beginning of the front surface, as shown in FIG. 3G. The semicylindrical shape of the left surface 304 and the right surface 306 has a radius $R_S$, as shown in FIG. 3C. In some examples, the radius $R_S$ is between about 1-2 inches. In other examples, the radius $R_S$ is between about 1.2 to about 1.8 inches. In yet further examples, the radius is $R_S$ is between about 1.4 to about 1.6 inches.

The front surface 302 is shaped substantially as two half-hemispheres connected by a partial semicylinder. One of the half-hemispheres is attached to the front of the left surface 304 and the other half-hemisphere is attached to the right surface 306. In some examples, the radius of the half-hemispheres $R_H$ is the same as the radius $R_S$ of the semicylindrical shape of the left surface 304 and the right surface 306, as shown in FIG. 3C. The two half-hemisphere shapes are connected by a partial semicylinder having a height $H_F$ defined by distance between the front-most points of the two half-hemisphere shapes of the front surface 302, as shown in FIG. 3C. The partial semicylinder has a curved surface, which forms the front edge of the bottom surface 318. Because of the curved surface of the partial semicylinder, the partial semicylinder has a variable radius $R_F$, with its maximum radius $R_{Fmax}$ occurring at the inner edges of the two half-hemisphere shapes and its minimum radius $R_{Fmin}$ occurring at the geometric center of the front surface 302, as shown in FIG. 3C.

The bottom surface 318 is a curved substantially smooth surface in the shape of an arc. As discussed above, the center point $C_B$ of the bottom surface 318 arc may be the same as the center point $C_I$ of the imaging arc. In such an example, the arc of the bottom surface 318 is concentric with the imaging arc. In another example, the curvature $(k_B)$ of the bottom surface 318 may be equal to the curvature $(k_I)$ of the imaging arc. In that example, the curvature $(k_B)$ of the bottom surface 318 is equal to the inverse of the arc radius $R_B$ of the bottom surface 318. In some examples, the curvature $(k_B)$ of the bottom surface, may be greater than or less than the curvature $(k_I)$ of the imaging arc. For instance, the ratio of the curvature $(k_B)$ of the bottom surface to the curvature $(k_I)$ of the imaging arc may be about 5:1 or greater. The bottom surface 318 is connected to the left surface 304, the right surface 306, the back surface 310, and the front surface 302.

The top surface 308 is a substantially planar surface connected to the left surface 304, the right surface 306, the back surface 310, and the front surface 302. In other examples, the top surface 308 may be a curved surface having a shape similar to the curved bottom surface 318. For instance, the top surface 308 may be arc-shaped with a center point of the top surface 308 arc being the same as the center point $C_I$ of the imaging system and the center point $C_B$ of the bottom surface 318. In such an example, the imaging arc, the arc of the top surface 308, and the arc of the bottom surface 318 are all concentric. Thus, the thickness of the compression element 300 remains consistent for a larger portion of the breast compression element 300 relative to the imaging source as it sweeps across the imaging arc. In other examples, the top surface 308 may have a curvature $(k_T)$ equal to that of the curvature $(k_B)$ of the bottom surface 318 and/or the curvature $(K_I)$ of the imaging arc.

The compression element 300 is substantially free from sharp edges. For example, the transitions between the surfaces of the compression element 300 may all be smooth and therefore free from sharp edges. The transition between the left surface 304 and the top surface 308 occurs at the location where the tangent plane to the semicylindrical shape of the left surface 304 intersects and is parallel to the plane of the of the top surface 308. Similarly, the transition between the right surface 306 intersects and the top surface 308 occurs at the location where the tangent plane to the semicylindrical shape of the right surface 306 is parallel to the plane of the of the top surface 308. The transition between the front surface 302 and the top surface 308 occurs where the tangent planes of the half-hemisphere shapes and the partial semicylinder shape of the front surface 302 intersect and are parallel with the plane of the top surface 308. The transitions between the front surface 302 and the left surface 304 and the right surface 306, respectively, also occur at locations where the tangent plane of the semicylindrical shapes of the left surface 304 and the right surface 306 intersect and are parallel to the tangent planes of the half-hemisphere shapes of the front surface 302. Further, the transition between the front surface 302 and the bottom surface 318 occurs at a location such that the curvature of the bottom edge of the front surface 302 matches the curvature of the bottom surface 318. The transition between the front surface 302 and the bottom surface 318 is also at a location where the tangent plane of the partial semicylinder shape of the front surface is parallel to the tangent plane of the curved bottom surface 318. The transitions between the bottom surface 318 and the left surface 304 and the right surface 306, respectively, also occur at locations where the tangent plane of the semicylindrical shapes of the left surface 304 and the right surface 306 intersect and are parallel to the tangent planes of the curved bottom surface 318. Accordingly, each those transitions are smooth and do not include any sharp edges.

The smooth surfaces and transitions between the surfaces provide for additional comfort of the patient and improved image quality. For instance, the smooth curved bottom surface 318 allows for a more comfortable compression procedure for the patient. The smooth transitions between the surfaces also increase the comfort of the patient, particularly in systems that involve tilting of the imaging system, such as depicted in FIG. 1C. In such systems, the chest wall of the patient is pressed against the front surface 302 of the compression element 300 could cause significant discomfort. The structure of the compression element 300 is also suited to support the weight of the patient that is applied to the compression element 300 during scanning in a tilted system.

The transitions between adjacent surfaces are described herein as smooth and substantially free from sharp edges. Sharp edges may cause areas of high stress on the shrink wrap that covers a significant portion of the breast compression element 300, thus increasing the likelihood of ripping. Further, sharp edges may also interfere with the x-ray radiation and cause discomfort for the patient. The smooth transitions reduce these undesired effects. In an example, a "sharp edge" may be defined as an intersection at a defined line or line segment of two essentially planar surfaces. In another example, a sharp edge may be defined as an edge between two surfaces where the angle between the tangent plane of the first surface and the tangent plane of the second surface is less than about 120 degrees at the location of intersection between first and second surfaces. For example, although majority of the various surfaces discussed above all intersect at location substantially free from sharp edges, the intersection between the back surface 310 and the back surfaces need not be a smooth transition. For instance, in the example depicted in FIGS. 3A-3I, the transition between the back surface 310 and the left surface 304, the right surface 306, the top surface 308, and the bottom surface 318 each include a sharp edge. As an example, as depicted, the plane of the back surface 310 is perpendicular to the plane of the top surface 308.

FIG. 3I depicts the flexible material 314 removed from the remainder of the breast compression element 300 for clarity.

In some examples, however, the flexible material 314 is not removable from the remainder of the compression element 300. For instance, where the flexible material 314 is a shrink-wrap material, the shrinking process is performed when the flexible material 314 is covering the remainder of the compression element 300. Thus, in such an example, the flexible material 314 is not easily removed.

In examples where the flexible material 314 is a shrink-wrap material or other similar tight-fitting material, the flexible material 314 may be applied to the compression element 300 prior to conducting a breast imaging procedure. Heat is then applied to the compression element 300 and the flexible material 314 to cause the flexible material to shrink and increase the tension of the portion of the flexible material 314 spanning the gap 316. In some examples, the heating process may occur at a time just prior to the breast imaging procedure in order to warm the breast compression element 300 to increase patient comfort as the breast is compressed. Additionally, the flexible material 314 is advantageously disposable. As such, after use with a first patient, the flexible material 314 may be removed and a new flexible material 314 may be applied for a subsequent patient. This may eliminate the need to clean or otherwise treat the surface of the breast compression element 300 between patients.

Figure 4A:
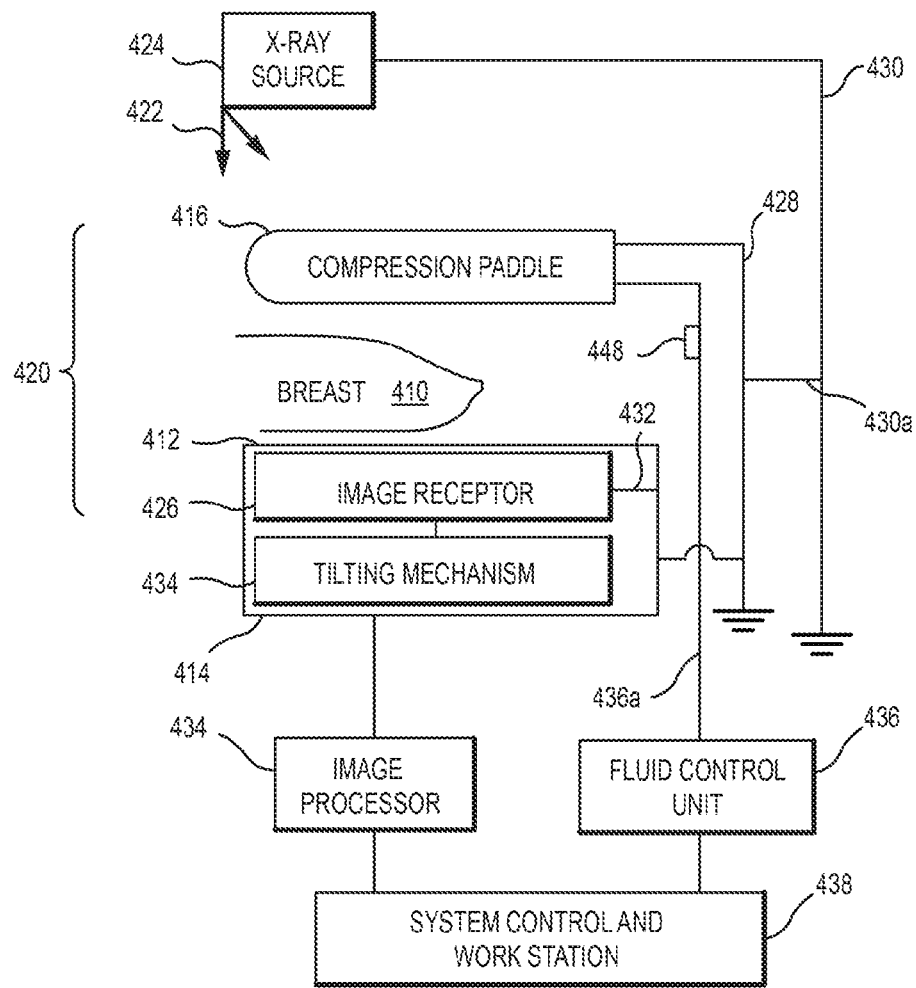
FIG. 4A depicts a schematic view of an imaging system using the breast compression element of FIGS. 3A-3I.
Figure 4B:
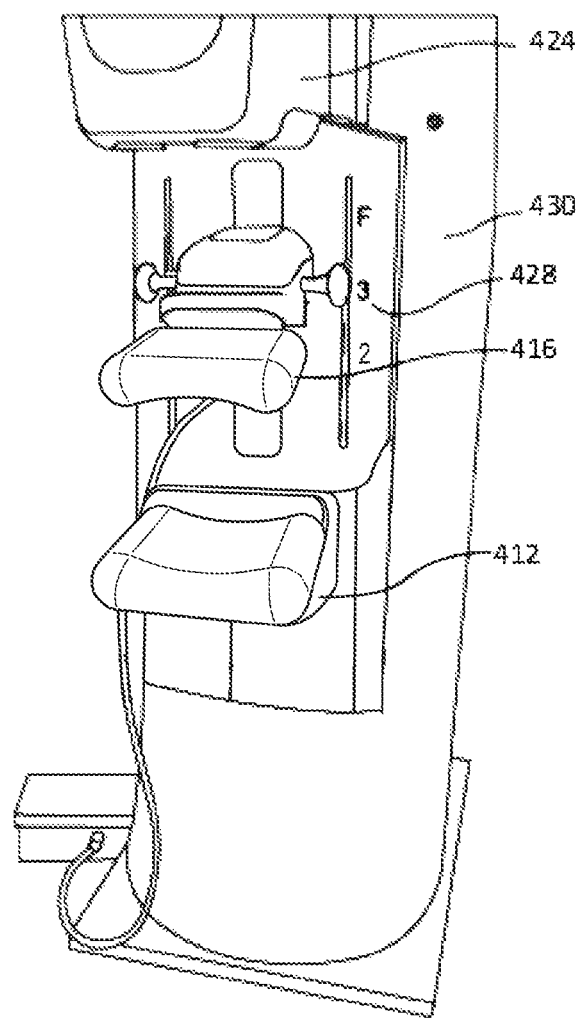
FIG. 4B depicts a perspective view of an imaging system of FIG. 4A.

FIG. 4A depicts a schematic view of an imaging system using the breast compression element of FIGS. 3A-3I. FIG. 4B depicts a perspective view of a breast imaging system of FIG. 4A and is described concurrently with FIG. 4A. In the depicted system, a patient's breast 410 is immobilized for x-ray imaging between two breast compression elements, namely a breast support platform 412 and a compression paddle 416. Platform 412 can be the upper surface of a housing 414. Either one or both of the platform 412 and the compression paddle 16 may be made in the shape of the of the breast compression element depicted in FIGS. 3A-3I. Platform 412 and paddle 416 form a breast immobilizer unit 20 that is in a path of an imaging beam 422 emanating from x-ray source 424. For instance, where the platform 412 incorporates the breast compression elements depicted in FIGS. 3A-3I, a radiographic detector or image receptor 426 may be incorporated into a hollow portion of the breast compression element. Beam 422 impinges on the image receptor 426 that is in housing 414, which in some examples may be at least a portion of the breast compression element. Immobilizer 420 and housing 414 are supported on an arm 428. X-ray source 424 is supported on an arm 430. For mammography, support arms 428 and 430 can rotate as a unit about an axis such as at 430a between different imaging orientations such as CC and MLO, so that the system can take a mammogram projection image at each orientation. Image receptor 426 remains in place relative to housing 414 while an image is taken. Immobilizer 420 releases breast 410 for movement of arms 428 and 430 to a different imaging orientation. For tomosynthesis, support arm 428 stays in place, with breast 410 immobilized and remaining in place, while at least source support arm 430 rotates source 424 relative to immobilizer 420 and breast 410 about an axis such as 30a. The system takes plural tomosynthesis projection images of breast 410 at respective angles of beam 422 relative to breast 410. Concurrently, image receptor 426 may be tilted relative to breast platform 412 in sync with the rotation of source support arm 430. The tilting can be through the same angle as the rotation of source 424, but may be through a different angle, selected such that beam 422 remains substantially in the same position on image receptor 426 for each of the plural images. The tilting can be about an axis 432a, which can but need not be in the image plane of image receptor 426. A tilting mechanism 434, which also is in housing 414 or is otherwise coupled with receptor 426, can drive image receptor 426 in a tilting motion. Axes 430a and 432a extend left-right as seen in FIG. 4A. For tomosynthesis imaging and/or CT imaging, breast platform 412 can be horizontal or can be at an angle to the horizontal, e.g., at an orientation similar to that for conventional MLO imaging in mammography. The system of FIGS. 4A-4B can be solely a mammography system, a CT system, or solely a tomosynthesis system, or a "combo" system that can perform multiple forms of imaging. An example of such a combo system is been offered by the assignee hereof under the trade name Selenia Dimensions.

When the system is operated, image receptor 426 produces imaging information in response to illumination by imaging beam 422, and supplies it to image processor 434 for processing to generate breast x-ray images. A fluid control unit 436 connects with the compression paddle to provide warm air into the compression paddle 416 to increase the comfort of the patient, and/or heat or pressurize the flexible material surrounding the paddle, as described heat. In an example, the fluid control unit 436 connects via a quick-release snap-on connection 448. A system control and work station unit 438 controls the operation of the system and interacts with a user to receive commands and deliver information including processed-ray images.

Image processing with a compression paddle having a non-planar compression surface, however, raises additional challenges due to the shape of the paddle. For instance, due to the shape of the paddle being non-planar or have in a non-uniformity on the compression surface, the breast is not compressed to a uniform thickness. Accordingly, radiation that passes through the curved paddle and the compressed breast is attenuated differently. As a result, bright spots and non-uniformity of the resultant image occurs. The present technology provides for a solution for processing an image when using a curved paddle to correct for the differences in attenuations. As an example, FIG. 5A shows an uncorrected image of a breast compressed with a curved paddle, such as those described herein or those cited in Publication No. WO 2014/176445, which is hereby incorporated herein by reference in its entirety. As can be seen from the image, the upper portion of the breast appears darker than normal and the center of the breast, particularly towards the chest wall, appears brighter than normal. By using the image processing techniques discussed herein, the image can be corrected to the corrected image shown in FIG. 5B. As can be seen from the image in FIG. 5B, the brightness appears more uniform and the underlying tissue composition of the can be more easily discerned.

In some examples, the image processing techniques of the present technology involves generating a correction map for a particular curved paddle having a non-planar compression surface. The generation of the correction map may only need to be performed once for a particular curved paddle shape and imaging system. For instance, the same correction map may be utilized for all systems of a given type using the particular curved paddle. Once a correction map has been generated for the particular curved paddle, the correction map can be applied to raw image data or an image dataset taken of a breast compressed with the particular curved paddle to generate a corrected image. The correction map may also be adjusted for a particular scan configuration, such as tomosynthesis imaging, two-dimensional imaging, CT imaging, mediolateral-oblique imaging, craniocaudal (CC) imaging, or other imaging configurations and orientations, including combinations thereof.

Figure 6A:
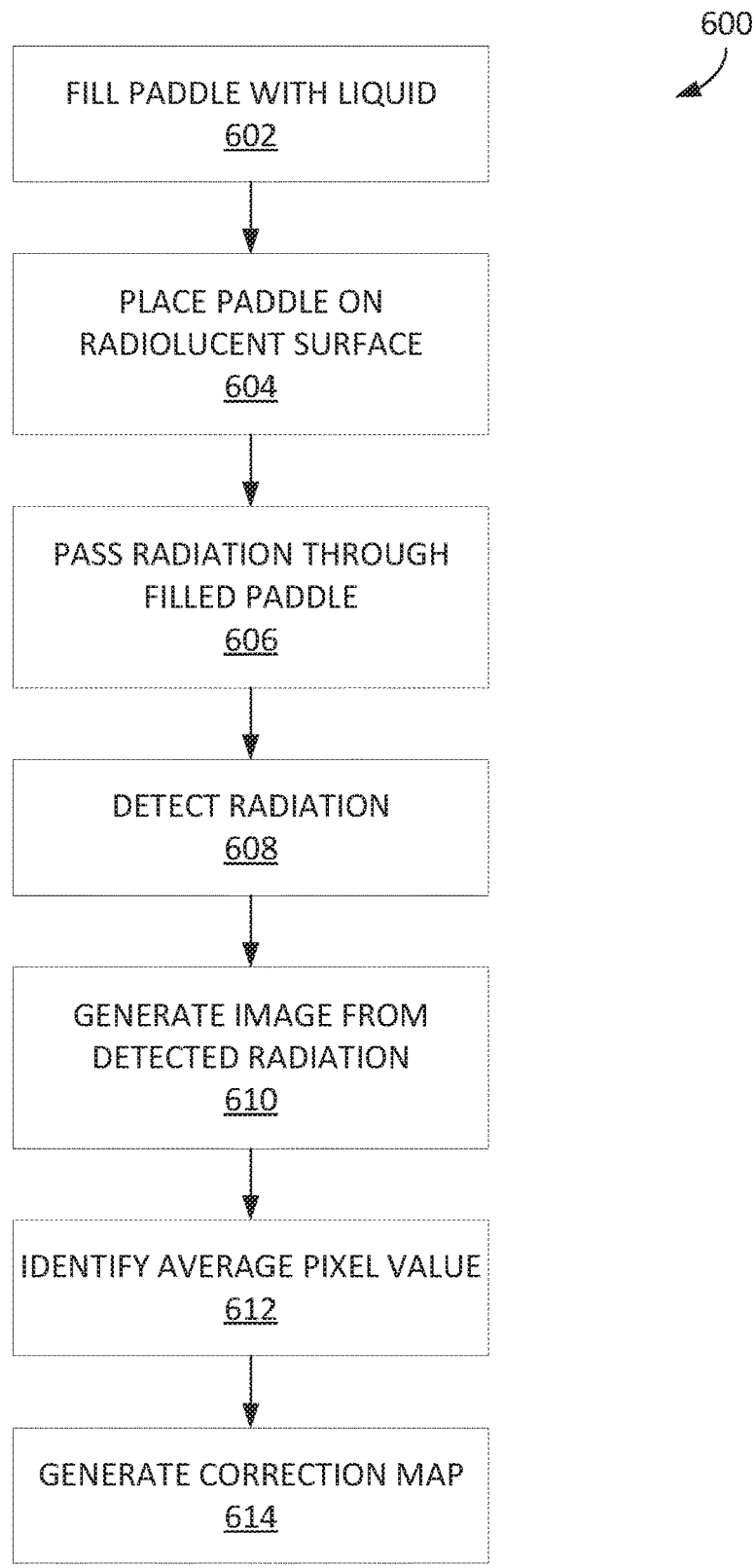
FIG. 6A depicts a method for generating a correction map for image processing for curved paddles.

FIG. 6A depicts a method 600 for generating a correction map for image processing for curved paddles. At operation 602, the paddle is filled with a liquid such as water. For instance, the paddle may be hollow and have an opening on the top of the paddle, among other positions, such that the paddle may be filled. For instance, the paddle may include a recess on at least a top portion of the paddle to receive the liquid. The recess may be generally open or may include an opening on a portion to access the recess. The recess may generally be on the top portion of the paddle such that the liquid may fill a portion which corresponds to the compression surface. Depending on the paddle, certain connection slots or other apertures in the paddle may need to be plugged such that the liquid does not flow out the paddle. For curved paddles that are not hollow, the paddle may be dipped in water in a substantially radiolucent container. At operation 604, the paddle is placed on a substantially radiolucent surface proximate to the detector. For instance, the paddle may be placed on a Lucite block having about generally a 4 centimeter thickness. In some examples, the substantially radiolucent surface covers the entire imaging area of the detector.

Figure 6C:
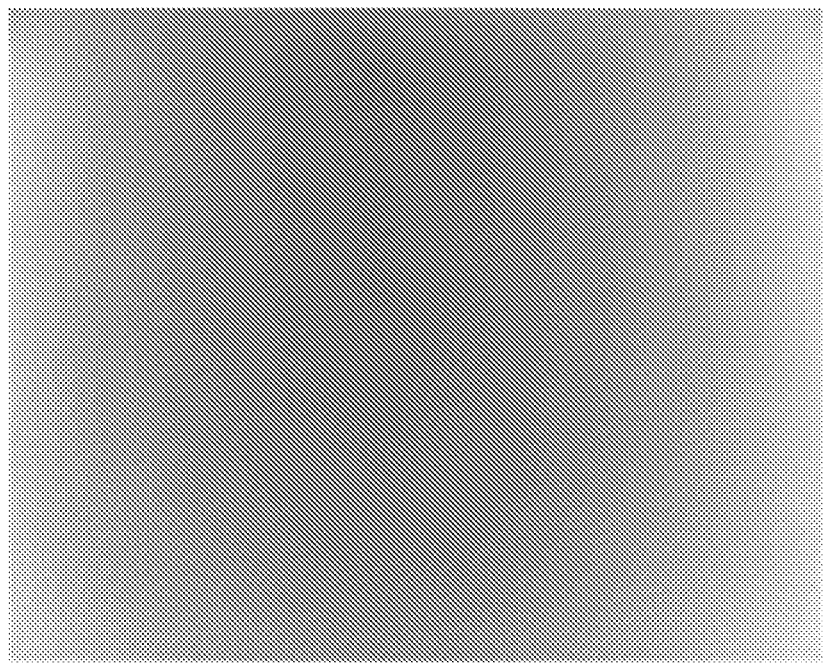
FIG. 6C depicts an example corrected image based on the sample correction map.
Figure 6B:
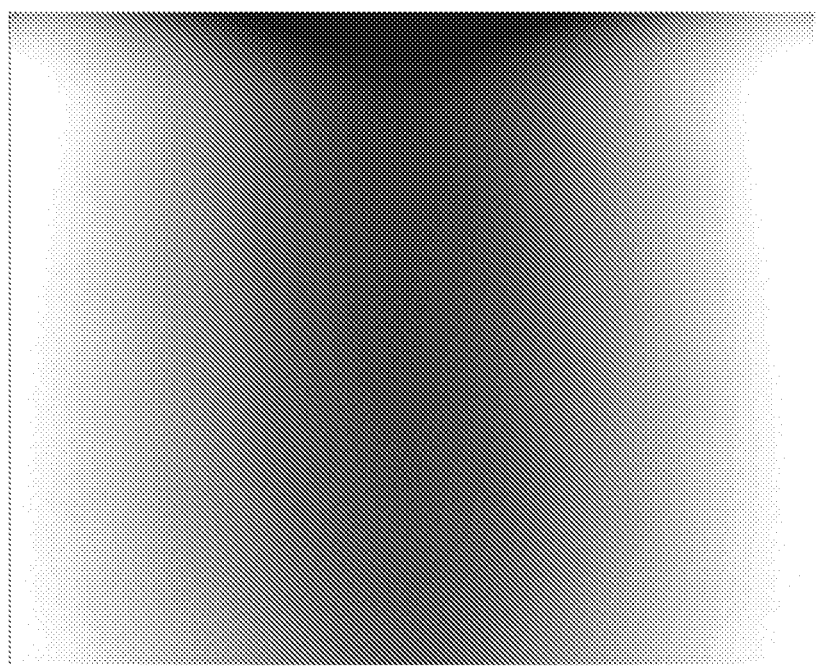
FIG. 6B depicts an example uncorrected image used for a sample correction map.

Radiation, such as x-ray radiation, is passed through the filled paddle and the substantially radiolucent surface at operation 606. The radiation is then detected by the detector at operation 608. The emission and detection of radiation may occur during a standard 2D imaging mode. In some examples, an auto-kV mode may be used, but other modes may also be suitable. The radiation used for calibration or generation of the correction map may be ay one or more of a scout exposure, a full mammographic exposure, or one or more tomosynthesis exposures. An image, or image data, is the generated form the detected radiation at operation 610. The image generated is indicative of the curved paddle shape. An example image produced at operation 610 is depicted in FIG. 6B.

From the image data produced in operation 610, an average pixel value is determined at operation 612. The average pixel value may be determined across the entire image. Based at least one average pixel value, the correction map is generated at operation 614. The correction map may be generated by dividing the pixel values of the image data generated in operation 610 by the average pixel value determined in operation 612 to generate a normalized correction map. In some examples, the correction map is further modified by generating a series of polynomial fits to represent the correction map. For instance, the correction map may be considered to be a matrix, where the elements of the matric represent correction values for a corresponding pixel of the detector. Each element of the matrix includes a value for scaling a brightness value of the corresponding pixel of the detector. Similarly, the correction map may also be considered to be a set of columns (x) of pixels or points and a rows (y) of pixels or points. In such an example, for each column (x), pixels along the rows (y) are selected. In selecting the pixels, some pixels may skipped, such as skipping by ten pixels for each selection. The values for the selected pixels are then fit to a polynomial function, such as a 4th order polynomial. For each of the y-values, the polynomial fitting may be used to generate a fitted image or a fitted correction map. The fitted correction map may also be smoothed using an averaging technique, such as a boxcar averaging method. In addition, the smoothed, fitted correction map may be scaled down. In some examples, the scaling may be by a factor of 4 and may be done using decimation (e.g., skipping points). Other scaling factors are contemplated. The scaled, smoothed, and fitted correction map may then be stored as a final correction map to be used in image processing. By fitting the correction map to a polynomial, image noise or other local irregularities are effectively removed from the final correction map. Once the correction map has been generated, it can be used to correct image data taken using the curved paddle for which the correction map was generated. For example, the image shown in FIG. 6C is a corrected version of the image shown in FIG. 6B using the correction map generated from the image in FIG. 6B.

Figure 7:
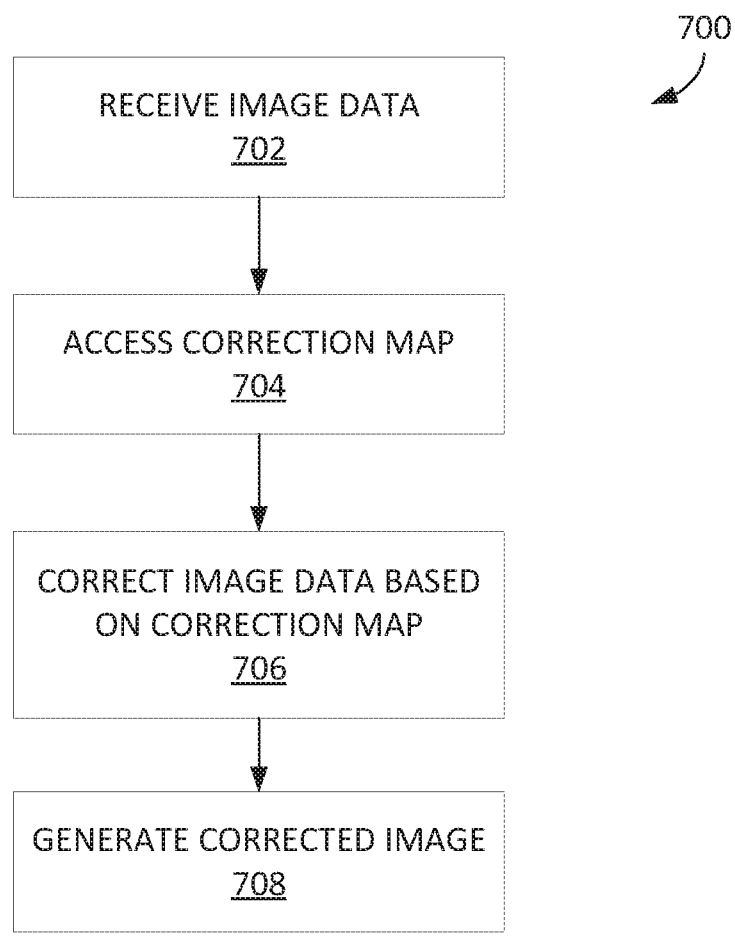
FIG. 7 depicts a method for image processing for curved paddles.

FIG. 7 depicts a method 700 for image processing for curved paddles utilizing a correction map, such as the one generated by method 600 depicted in FIG. 6A. At operation 702, image data is received. The image data may be received from detector of the imaging system. At operation 704, a correction map associated with the compression paddle is used to compress the breast during imaging. In some examples, the correction map may be stored locally or remotely from the imaging system. The correction map may be further altered or corrected prior to its use in correcting the image data received in operation 702. For example, the correction map may be scaled based on an image size for the image data received in operation 702. The scaling may be to upscale the correction map to the current image size using a linear interpolation technique. The correction map may also be smoothed using an averaging technique, such as a boxcar averaging technique. The correction map may also be modified by applying a squeeze factor. The squeeze factor is an adjustment to the correction map that is paddle dependent. The squeeze factor allows for adjustment of the magnitude of the correction provided by the correction map. The correction map may also be modified to correct for a projection angle and a paddle shift. Such a correction shifts the correction map depending on the projection angle and the actual paddle shift. In addition, the correction map may also be modified to correct for magnification. For example, the correction map may be modified based on the paddle height used for imaging as compared to the paddle height used during calibration. For instance, in examples where a 4 cm Lucite block is used as the substantially radiolucent surface in operation 604 of the calibration method 400, the calibration height is 4 cm. The height may be measured to any point on the paddle as long as the measurement is consistent when comparing heights.

At operation 706, the image data received at operation 702 is corrected based on the correction map accessed in operation 704. In some examples, the image data is corrected based on the correction map as modified according to the techniques discussed above. The image data may be corrected on a pixel-by-pixel basis. The image may be corrected by multiplying or dividing the image data by the correction map. For instance, each pixel of the image data may be multiplied or divided by the corresponding pixel value in the correction map. The correction to the image data may also be a correction to the raw image data prior to generating an actual image of the breast being imaged. At operation 708, a corrected image is generated from the corrected image data. In sonic examples, such as with breast CT and/or tomosynthesis techniques, the corrected image may be part of an image dataset that includes a series of images. Generating the corrected image may also include displaying the corrected image on a display screen or other medium for viewing and analysis by a physician or technician.

In some instances, further correction to the image data may be desired for image areas near the chest wall, such as about 2 cm from the chest wall. For example, while the above corrections work well for imaging portions of the breast in contact with the paddle, the corrections may be further improved for portions of the breast not in contact with the paddle. When the breast is not in contact with the paddle, an air gap is formed between the breast and the paddle. The x-ray attenuation is therefore different for portions of the breast in contact with the paddle and portions of the breast not in contact with the paddle. Portions of the breast not in contact with the paddle generally occur near the chest wall. The additional correction for imaging the breast portions not in contact with the paddle may be referred to as an air area correction (AAC).

The AAC may be a further correction in addition to already utilized corrections or other image processing techniques to further help visualize the breast. As an example, the AAC may be a further correction to at least one of a multiscale image decomposition technique utilized in processing the image and skin line detection or correction techniques. For instance, the skin line correction may be utilized to equalize the pixel values near the skin edge in order to improve visualization of the breast near the skin line. The AAC may be an additional correction near the chest wall to correct for the brightness changes due to the air gap between the paddle and the breast. As an example, the AAC may utilize a correction based on the difference between the pixel value and a threshold value. For instance, the adjustment value may be based on a value, representing the difference between the pixel value and a threshold value, multiplied by a slope value at one or more image decomposition scales. In addition, the slope may be represented by a weighting factor function based on the pixel location. After the AAC correction according to the above techniques, the attenuation in the small local vertical area near the chest wall is corrected and the final processed images do not appear as having a non-uniformity, such as a slightly dark area, near the chest wall.

Figure 8:
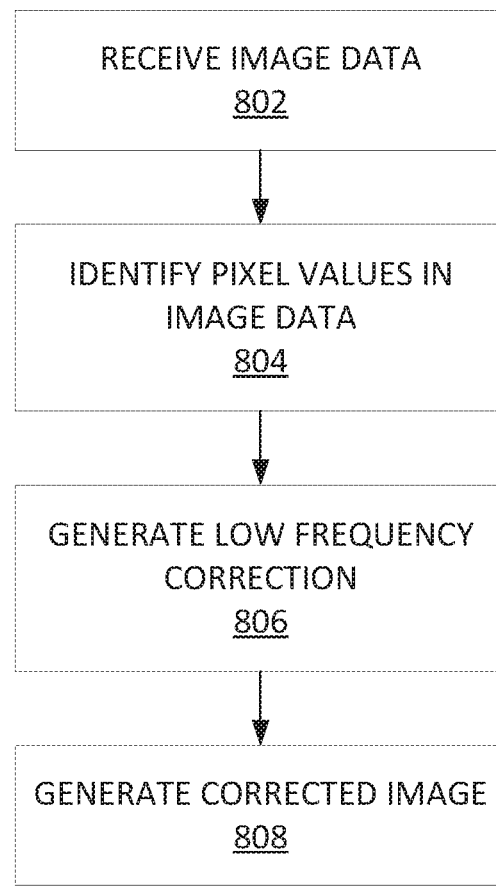
FIG. 8 depicts a method for image processing for a paddle providing inconsistent compression.

FIG. 8 depicts a method for image processing for a paddle providing inconsistent compression. For example, with a paddle having a flexible element, such as breast compression element 300 discussed above, each breast will not be compressed in the same manner. Accordingly, additional improvements may be made in addition to the one-time calibration map solution discussed above. For example, correction to the images taken with a paddle providing inconsistent compression may be determined on the fly for each image taken of the breast.

At operation 802, image data is received for an image of the breast. The image data may be received from a detector. At operation 804, pixel values in the image data are identified. In some examples, an average pixel value may also be determined. Based on the pixel values in the image data, a low frequency correction is determined at operation 806. The low frequency correction may be generated in the form of a correction map or a low frequency function. The low frequency correction is to correct for the background variations in brightness, while not Obscuring any of the higher detail elements of the image, such as vascular elements or other tissue composition of the breast. Based on the low frequency correction, a corrected image may then be generated in operation 808.

Figure 9:
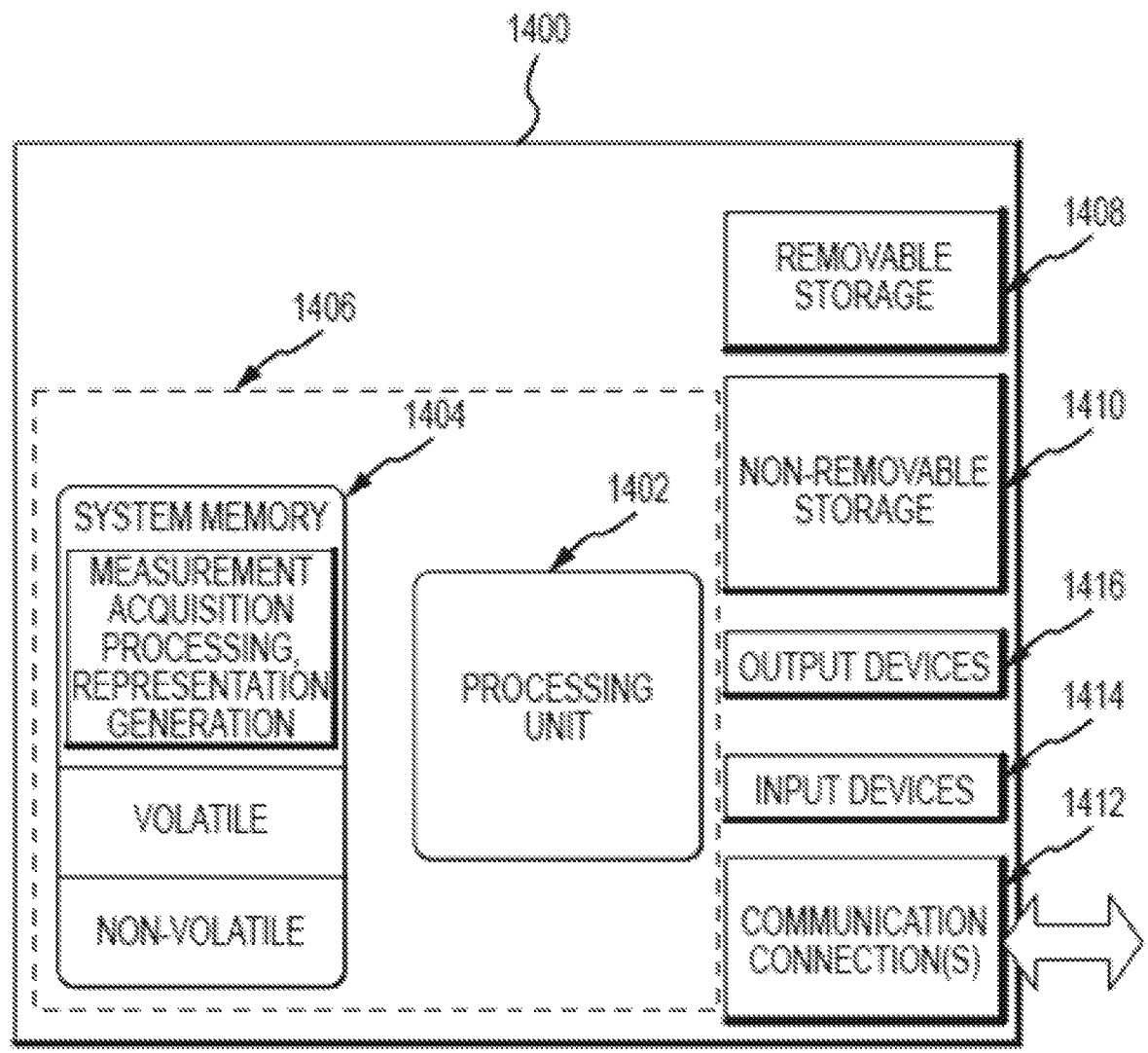
FIG. 9 depicts one example of a suitable operating environment in which one or more of the present examples can be implemented.

FIG. 9 depicts one example of a suitable computing device 1400 that may be coupled to the scanning systems discussed herein. The computing device 1400 is a suitable operating environment in which one or more of the present examples can be implemented. This operating environment may be incorporated directly into a scanning system, or may be incorporated into a computer system discrete from, but used to control or process data from, the scanning systems described herein. This is only one example of a suitable operating environment and is not intended to suggest any limitation as to the scope of use or functionality. Other well-known computing systems, environments, and/or configurations that can be suitable for use include, but are not limited to, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 1400 typically includes at least one processing unit 1402 and memory 1404. Depending on the exact configuration and type of computing device, memory 1404 (storing, among other things, instructions to perform the measurement acquisition, processing, and visual representation generation methods disclosed herein) can be volatile (such as RAM), non-volatile (such as ROM, flash memory, etc.), or some combination of the two. This most basic configuration is illustrated in FIG. 9 by dashed line 1406. Further, environment 1400 can also include storage devices (removable, 1408, and/or non-removable, 1410) including, but not limited to, solid-state devices, magnetic or optical disks, or tape. Similarly, environment 1400 can also have input device(s) 1414 such as touch screens, keyboard, mouse, pen, voice input, etc., and/or output device(s) 1416 such as a display, speakers, printer, etc. Also included in the environment can be one or more communication connections 1412, such as LAN, WAN, point to point, Bluetooth, RF, etc.

Operating environment 1400 typically includes at least some form of computer readable media. Computer readable media can be any available media that can be accessed by processing unit 1402 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible and non-transitory medium which can be used to store the desired information.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 1400 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in hospitals, offices, enterprise-wide computer networks, intranets and the Internet.

In some examples, the components described herein comprise such modules or instructions executable by computer system 1400 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some examples, computer system 1400 is part of a network that stores data in remote storage media for use by the computer system 1400.

Figure 10:
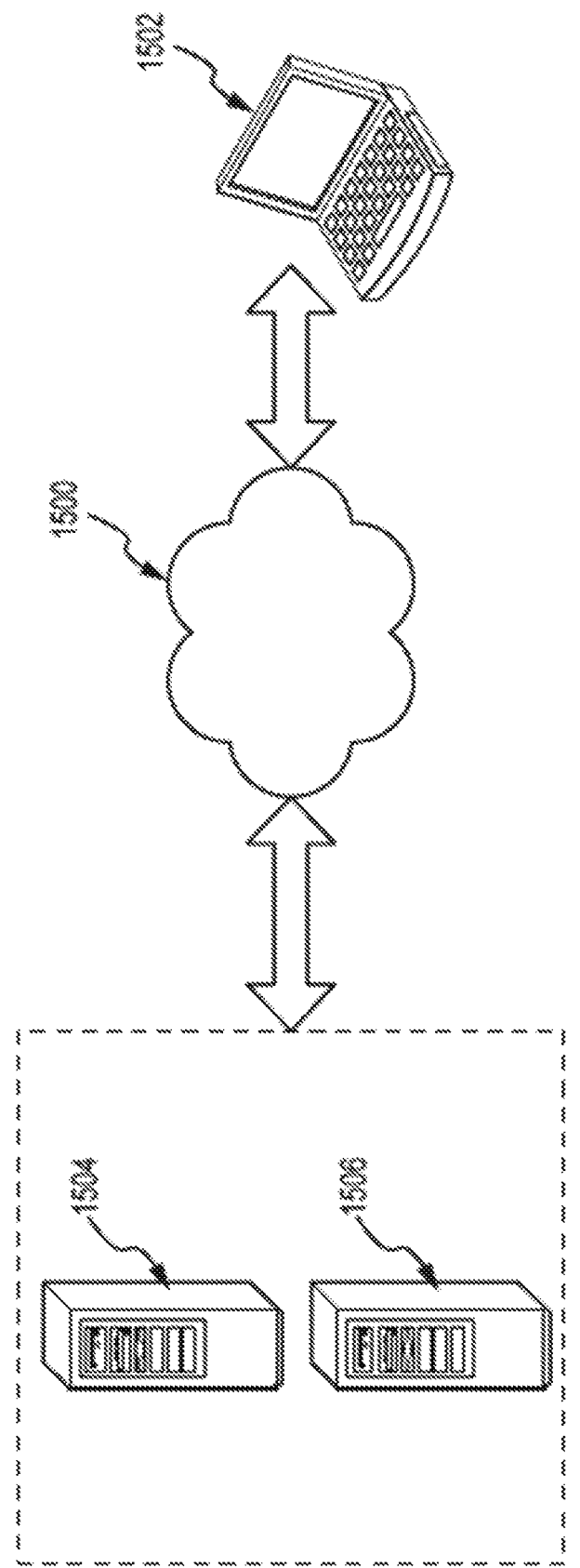
FIG. 10 depicts an example of a network in which the various systems and methods disclosed herein may operate.

FIG. 10 is an example of a network 1500 in which the various systems and methods disclosed herein may operate. In examples, a client device, such as client device 1502, may communicate with one or more servers, such as servers 1504 and 1506, via a network 1508. In examples, a client device may be a laptop, a personal computer, a smart phone, a PDA, a netbook, or any other type of computing device, such as the computing device in FIG. 9. In examples, servers 1504 and 1506 may be any type of computing device, such as the computing device illustrated in FIG. 9. Network 1508 may be any type of network capable of facilitating communications between the client device and one or more servers 1504 and 1506. Examples of such networks include, but are not limited to, LANs, WANs, cellular networks, and/or the Internet.

In examples, processing of data and performance of the methods described herein may be accomplished with the use of one or more server devices. For example, in one example, a single server, such as server 1504 may be employed to assist in processing data and performing the methods disclosed herein. Client device 1502 may interact with server 1504 via network 1508. In further examples, the client device 1502 may also perform functionality disclosed herein, such as scanning and processing data, which can then be provided to servers 1504 and/or 1506.

In alternate examples, the methods disclosed herein may be performed using a distributed computing network, or a cloud network. In such examples, the methods disclosed herein may be performed by two or more servers, such as servers 1504 and 1506. Although a particular network example is disclosed herein, one of skill in the art will appreciate that the systems and methods disclosed herein may be performed using other types of networks and/or network configurations. Further, the data sent to the servers and received from the servers may be encrypted. The data may also be stored in an encrypted manner both locally and on the servers.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A system for imaging a breast, the system comprising:
   a radiation source;
   at least one compression paddle having a non-planar compression surface, wherein the at least one compression paddle is configured to compress the breast during imaging of the breast;
   a detector configured to detect radiation emitted from the radiation source after passing through the at least one compression paddle and the breast, wherein the detector includes a plurality of pixels; and
   a memory and a processor operatively connected to the detector, wherein the memory stores instructions that, when executed by the processor, perform a set of operations, the operations comprising:
   receiving image data from the detector;
   accessing a correction map for the at least one compression paddle;
   correcting the image data based on the correction map to generate a corrected image data; and
   generating an image of the breast based on the corrected image data.

2. The system of claim 1, wherein the operations further comprise at least two of the following operations:
   upscaling the correction map based on an image size for the image;
   modifying the correction map by applying a squeeze factor;
   modifying the correction map for a projection angle and a paddle shift; and
   modifying the correction map based on a magnification.

3. The system of claim 2, wherein modifying the correction map based on magnification is based at least in part on a height of the compression paddle.

4. The system of claim 1, wherein the correction map is represented as a matrix, wherein the elements of the matrix represent correction values for a corresponding pixel of the detector.

5. The system of claim 4, wherein the elements of the matrix include values for scaling a brightness value of the corresponding pixel of the detector.

6. The system of claim 1, wherein correcting the image data includes correcting the image data on a pixel-by-pixel level.

7. The system of claim 1, wherein the operations further comprise further correcting a chest-wall area of the image representative of an area within about 2 cm of a chest wall.

8. The system of claim 7, wherein correcting the chest-wall area of the image includes determining a delta value based on at least slope value and a threshold value.

9. The system of claim 1, wherein the correction map is generated by a process comprising:
   filling the compression paddle with a liquid to create a filled paddle;

placing the filled paddle on a substantially radiolucent surface, wherein the radiolucent surface covers an imaging area of a detector;
passing radiation through the filled paddle and substantially radiolucent surface;
detecting the radiation passed through the filled paddle and substantially radiolucent surface;
generating a correction image based on the detected radiation;
identifying an average pixel value over the correction image; and
generating the correction map by dividing each pixel in the correction image by the average pixel value.

10. The system of claim 9, wherein generating the correction map further comprises generating a series of polynomial fits to represent the correction map.

* * * * *